US010537628B2

(12) United States Patent
Reddy et al.

(10) Patent No.: US 10,537,628 B2
(45) Date of Patent: Jan. 21, 2020

(54) RECOMBINANT TURKEY HERPESVIRUS VACCINES AND USES THEREOF

(71) Applicant: The Texas A&M University System, College Station, TX (US)

(72) Inventors: Sanjay M. Reddy, College Station, TX (US); Blanca M. Lupiani, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/228,912

(22) Filed: Aug. 4, 2016

(65) Prior Publication Data

US 2017/0043006 A1    Feb. 16, 2017

Related U.S. Application Data

(60) Provisional application No. 62/203,305, filed on Aug. 10, 2015.

(51) Int. Cl.
| | | |
|---|---|---|
| *A61K 39/12* | (2006.01) | |
| *C12N 7/00* | (2006.01) | |
| *C12N 15/86* | (2006.01) | |
| *A61P 31/12* | (2006.01) | |
| *A61K 39/00* | (2006.01) | |

(52) U.S. Cl.
CPC .............. *A61K 39/12* (2013.01); *A61P 31/12* (2018.01); *C12N 7/00* (2013.01); *C12N 15/86* (2013.01); *A61K 2039/5256* (2013.01); *A61K 2039/552* (2013.01); *C12N 2710/16322* (2013.01); *C12N 2710/16334* (2013.01); *C12N 2710/16343* (2013.01); *C12N 2710/16371* (2013.01); *C12N 2720/10022* (2013.01); *C12N 2720/10034* (2013.01); *C12N 2720/10071* (2013.01)

(58) Field of Classification Search
None
See application file for complete search history.

(56) References Cited

U.S. PATENT DOCUMENTS

| | | | |
|---|---|---|---|
| 5,980,906 | A | 11/1999 | Audonnet et al. |
| 6,045,803 | A | 4/2000 | Audonnet et al. |
| 2011/0212518 | A1 | 9/2011 | Singh et al. |
| 2013/0101619 | A1 | 4/2013 | Cook et al. |
| 2013/0230556 | A1* | 9/2013 | Sondermeijer ...... A61K 39/145 424/209.1 |

FOREIGN PATENT DOCUMENTS

| | | |
|---|---|---|
| CN | 103589693 A | 2/2014 |
| WO | WO 2013/082327 A1 | 6/2013 |

OTHER PUBLICATIONS

Ren et al., Biotechnol Lett. Aug. 2009;31(8):1159-65. abstract only.*
Morimoto et al. Microbiol Immunol 2009 vol. 53, pp. 155-161.*
Zelnik et al. (J Gen Virol 1995 vol. 76, pp. 2903-2907.*
International Search Report and Written Opinion for PCT/US2016/045577 dated Dec. 15, 2016.
Lupiana et al. "Generation of a bacterial artificial chromosome of CVRM strain to express VP2 gene of infectious bursal disease virus," American Association of Avian Pathologists, Chicago, Jul. 19-23, 2013.
Campbell et al., "KSHV episomes reveal dynamic chromatin loop formation with domain-specific gene regulation," *Nature Communications* 9:49, 2018.
Davison, "Evolution of the herpesviruses," *Veterinary Microbiology* 86:69-88, 2002.
Fuchs et al., "Identification and Characterization of the Pseudorabies Virus UL3.5 Protein, Which Is Involved in Virus Egress," *Journal of Virology* 70(6):3517-3527, 1996.
Morimoto et al., "Identification of multiple sites suitable for insertion of foreign genes in herpes simplex virus genomes," *Microbiol. Immunol.* 53:155-161, 2009.
Ren et al., "Construction of a recombinant BHV-1 expressing the VP1 gene of foot and mouth disease virus and its immunogenicity in a rabbit model," *Biotechnol. Lett.* 31:1159-1165, 2009.
Schikora et al., "The Bovine Herpesvirus Type 1 UL3.5 Open Reading Frame Encodes a Virion Structural Protein," *Virology* 240:76-82, 1998.
Spatz et al., "Molecular characterization of the complete genome of falconid herpesvirus strain S-18," *Virus Research* 188:109-121, 2014.
Zelnik et al., "Structure and properties of a herpesvirus of turkeys recombinant in which US1, US10 and SORF3 genes have been replaced by a lacZ expression cassette," *Journal of General Virology* 76:2903-2907, 1995.
European Extended Search Report regarding European Application No. 16835663, dated Mar. 25, 2019.

* cited by examiner

*Primary Examiner* — Shanon A. Foley
*Assistant Examiner* — Myron G Hill
(74) *Attorney, Agent, or Firm* — Dentons US LLP

(57) ABSTRACT

The present disclosure provides a recombinant viral vector comprising at least one transgene inserted into a Marek's disease viral genome for treatment of diseases in poultry. Also provided are immunogenic compositions comprising such recombinant viral vectors and methods for preventing or inhibiting Marek's disease in combination with at least a second disease in poultry.

29 Claims, 5 Drawing Sheets

Specification includes a Sequence Listing.

FIG. 1

NheI -------- VP2 -------- XbaI*/EcoRI PstI EcoRV BstXI NotI XhoI NsiI XbaI pCR 2.1 Topo TA cloning vector sequences are indicated in grey shading.

* XbaI site present in the primer sequence at the end of the VP2 gene was not functional due to methylation of the bacterial strain used.

FIG. 2

NheI -------- VP2 -------- XbaI*/EcoRI/PstI/EcoRV/BstXI/NotI/XhoI/NsiI/XbaI/DraI/ApaI/PmeI pcDNA3.1 vector sequences are indicated in grey shading.

FIG. 3

NheI ------VP2------PciI------BamHI------XbaI*/EcoRI/PstI/EcoRV/BstXI/NotI/XhoI/NsiI/XbaI

PciI and BamHI sequences shaded grey correspond to the VP2 2512 synthetic gene fragment.

FIG. 4

SpeI EcoRI ----- HVT left arm ----- HincII ----- HVT right arm ----- EcoRI PstI EcoRV pCR 2.1 Topo TA vector sequences are indicated by grey shading.

FIG. 5

Spe EcoRI --- HVT left arm --- VP2 E2512 expression cassette --- HVT right arm --- EcoRI PstI pCR Topo TA vector sequences are indicated by grey shading.

Spe EcoRI --- HVT left arm (507 bp) --- Human CMV promoter/NheI --- VP2 E2512 --- XbaI/Bovine growth hormone polyA signal --- HVT right arm (763 bp) --- EcoRI PstI pCR Topo TA vector sequences are indicated by grey shading.

SEQUENCE LISTING

<160> NUMBER OF SEQ ID NOS: 22

<210> SEQ ID NO 1
<211> LENGTH: 36
<212> TYPE: DNA
<213> ORGANISM: Artificial Sequence
<220> FEATURE:
<223> OTHER INFORMATION: Primer

<400> SEQUENCE: 1
gatcgctagc accatgacaa acctgcaaga tcaaac                36

<210> SEQ ID NO 2
<211> LENGTH: 38
<212> TYPE: DNA
<213> ORGANISM: Artificial Sequence
<220> FEATURE:
<223> OTHER INFORMATION: Primer

<400> SEQUENCE: 2
gatctctaga tcactacctc cttatggccc ggattatg              38

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
aactgacaga tacaatacg                                   19

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
cagcggatca attatatact                                  20

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
cgatgtacgg gccagatata c                                21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
tccccagcat gcctgctatt g                                21

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
gcagccgatg actaccagt                                                        19

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
ttgctgacca tgacatttgg t                                                     21

<210> SEQ ID NO 9
<211> LENGTH: 26
<212> TYPE: DNA
<213> ORGANISM: Artificial Sequence
<220> FEATURE:
<223> OTHER INFORMATION: Primer

<400> SEQUENCE: 9
gctagcatgg gctccagacc ttctac                                                26

<210> SEQ ID NO 10
<211> LENGTH: 53
<212> TYPE: DNA
<213> ORGANISM: Artificial Sequence
<220> FEATURE:
<223> OTHER INFORMATION: Primer

<400> SEQUENCE: 10
tctagatcac attttttgtag tggctctcat ctgatcgaga gtattcccaa gcc                 53

<210> SEQ ID NO 11
<211> LENGTH: 31
<212> TYPE: DNA
<213> ORGANISM: Artificial Sequence
<220> FEATURE:
<223> OTHER INFORMATION: Primer

<400> SEQUENCE: 11
gatatctcta gaatggaccg cgccgttagc c                                          31

<210> SEQ ID NO 12
<211> LENGTH: 32
<212> TYPE: DNA
<213> ORGANISM: Artificial Sequence
<220> FEATURE:
<223> OTHER INFORMATION: Primer

<400> SEQUENCE: 12
gatatctcta gactagccag acctggcttc tc                                         32

<210> SEQ ID NO 13
<211> LENGTH: 105
<212> TYPE: DNA
<213> ORGANISM: Artificial Sequence
<220> FEATURE:
<223> OTHER INFORMATION: Primer

<400> SEQUENCE: 13
cattctagat ccgcttccag gtccagggtt ctcctccacg tctccagcct gcttcagcag           60

```
gctgaagtta gtagctccgc ttcccatttt tgtagtggct ctcat              105
```

<210> SEQ ID NO 14
<211> LENGTH: 1362
<212> TYPE: DNA
<213> ORGANISM: Infectious bursal disease virus

<400> SEQUENCE: 14

```
atgacaaacc tgcaagatca aacccaacag attgttccgt tcatacggag ccttctgatg    60
ccaacaaccg gaccggcgtc catcccggac gacaccctgg agaagcacac tctcaggtca   120
gagacctcga cctacaattt gactgtgggg gacacagggt cagggctaat tgtctttttc   180
cctggattcc ctggctcaat tgtgggtgct cactacacac tgcagagcaa tgggaactac   240
aagttcgatc agatgctcct gactgcccag aacctaccgg ccagttacaa ctactgcagg   300
ctagtgagtc ggagtctcac agtgaggtca agcacactcc tggtggcgt ttatgcacta   360
aacggcacca taaacgccgt gaccttccaa ggaagcctga gtgaactgac agatgttagc   420
tacaatgggt tgatgtctgc aacggccaac atcaacgaca aaattgggaa tgtcctggta   480
ggggaggggg tcaccgtcct cagcttaccc acatcatatg atcttgggta tgtgaggctt   540
ggtgacccca ttcctgctat agggcttgac ccaaaaatgg tagccacatg tgacagcagt   600
gacaggccca gagtctacac cataactgca gccgatgact accagttctc atcacagtac   660
caaccaggtg gggtaacaat cacactgttc tcagccaaca ttgatgctat tacaagcctc   720
agcgttgggg gagagctcgt gtttcaaaca gcgttcaag ccttgtact gggcgccacc   780
atctaccttga taggctttga tgggactacg gtaatcacca gggctgtggc cgcagacaat   840
gggctgacgg ccggcaccga caatcttatg ccattcaata ttgtgattcc aaccaacgag   900
ataacccagc caattacatc catcaaactg agatagtga cctccaaaag tggtggtcag   960
gcgggggacc aaatgtcatg gtcagcaagt gggagcctag cagtgacgat ccacggtggc  1020
aactatccag ggcccctccg tcccgtcaca ctagtagcct acgaaagagt ggcaacagga  1080
tccgtcgtta cggtcgccgg ggtgagcaac ttcgagctga tcccaaatcc tgaactagca  1140
aagaacctgg ttacagaata cggccgattt gacccaggag ccatgaacta cacaaaattg  1200
atactgagtg agagggaccg tcttggcatc aagaccgtct ggccaacaag ggagtacact  1260
gactttcgtg agtacttcat ggaggtggcc gacctcaact ctcccctgaa gattgcagga  1320
gcatttggct tcaaagacat aatccgggcc ataaggaggt ag                     1362
```

<210> SEQ ID NO 15
<211> LENGTH: 454
<212> TYPE: PRT
<213> ORGANISM: Infectious bursal disease virus

<400> SEQUENCE: 15

```
Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80
```

```
Lys Phe Asp Gln Met Leu Leu Thr Ala Gln Asn Leu Pro Ala Ser Tyr
             85                  90                  95

Asn Tyr Cys Arg Leu Val Ser Arg Ser Leu Thr Val Arg Ser Ser Thr
        100                 105                 110

Leu Pro Gly Gly Gly Val Tyr Ala Leu Asn Gly Thr Ile Asn Ala Val
    115                 120                 125

Thr Phe Gln Gly Ser Leu Ser Glu Leu Thr Asp Val Ser Tyr Asn Gly
130                 135                 140

Leu Met Ser Ala Thr Ala Asn Ile Asn Asp Lys Ile Gly Asn Val Leu
145                 150                 155                 160

Val Gly Glu Gly Val Thr Val Leu Ser Leu Pro Thr Ser Tyr Asp Leu
                165                 170                 175

Gly Tyr Val Arg Leu Gly Asp Pro Ile Pro Ala Ile Gly Leu Asp Pro
                180                 185                 190

Lys Met Val Ala Thr Cys Asp Ser Ser Asp Arg Pro Arg Val Tyr Thr
            195                 200                 205

Ile Thr Ala Ala Asp Asp Tyr Gln Phe Ser Ser Gln Tyr Gln Pro Gly
    210                 215                 220

Gly Val Thr Ile Thr Leu Phe Ser Ala Asn Ile Asp Ala Ile Thr Ser
225                 230                 235                 240

Leu Ser Val Gly Gly Glu Leu Val Phe Gln Thr Ser Val Gln Gly Leu
                245                 250                 255

Val Leu Gly Ala Thr Ile Tyr Leu Ile Gly Phe Asp Gly Thr Thr Val
                260                 265                 270

Ile Thr Arg Ala Val Ala Ala Asp Asn Gly Leu Thr Ala Gly Thr Asp
            275                 280                 285

Asn Leu Met Pro Phe Asn Ile Val Ile Pro Thr Asn Glu Ile Thr Gln
    290                 295                 300

Pro Ile Thr Ser Ile Lys Leu Glu Ile Val Thr Ser Lys Ser Gly Gly
305                 310                 315                 320

Gln Ala Gly Asp Gln Met Ser Trp Ser Ala Ser Gly Ser Leu Ala Val
                325                 330                 335

Thr Ile His Gly Gly Asn Tyr Pro Gly Ala Leu Arg Pro Val Thr Leu
            340                 345                 350

Val Ala Tyr Glu Arg Val Ala Thr Gly Ser Val Val Thr Val Ala Gly
    355                 360                 365

Val Ser Asn Phe Glu Leu Ile Pro Asn Pro Glu Leu Ala Lys Asn Leu
370                 375                 380

Val Thr Glu Tyr Gly Arg Phe Asp Pro Gly Ala Met Asn Tyr Thr Lys
385                 390                 395                 400

Leu Ile Leu Ser Glu Arg Asp Arg Leu Gly Ile Lys Thr Val Trp Pro
                405                 410                 415

Thr Arg Glu Tyr Thr Asp Phe Arg Glu Tyr Phe Met Glu Val Ala Asp
            420                 425                 430

Leu Asn Ser Pro Leu Lys Ile Ala Gly Ala Phe Gly Phe Lys Asp Ile
    435                 440                 445

Ile Arg Ala Ile Arg Arg
    450

<210> SEQ ID NO 16
<211> LENGTH: 3641
<212> TYPE: DNA
<213> ORGANISM: Artificial Sequence
<220> FEATURE:
<223> OTHER INFORMATION: Transfer vector
```

<400> SEQUENCE: 16

```
aactgacaga tacaatacgg agagatttga ggcattcgct ggcaaagttt accatcgcct      60
gtactaagac gtcttctttt tcatcatcga atgctactag aaaaactcga ggtagaattt     120
cgcataggaa ttttcagagt aataagagct tacaaatgtt tatattgtgt aggcgtgcac     180
atgccaaaca cattcgagct caattgcagt ctgtaatcca agcccgcaaa ccccgtaaat     240
attacactcg cgcagtagat ggtagtacac gtccagtagt accggtcttc gtatacgagt     300
ttacagctat agacactgtt agtttacaca gagataacgt gatagagata gacgccccga     360
acccttgatt tcaacttgtg ggatgttcgt cgtatcggca acattggcat ccgctgcgga     420
ttatgtggac tttgcacgta ccaaccagaa cgttgcacga aagctgcgga atatgctccg     480
gtacaaggcc gggcgaatgg agatggtccg atgtacgggc cagatatacg cgttgacatt     540
gattattgac tagttattaa tagtaatcaa ttacggggtc attagttcat agcccatata     600
tggagttccg cgttacataa cttacggtaa atggcccgcc tggctgaccg cccaacgacc     660
cccgcccatt gacgtcaata atgacgtatg ttcccatagt aacgccaata gggactttcc     720
attgacgtca atgggtggag tatttacggt aaactgccca cttggcagta catcaagtgt     780
atcatatgcc aagtacgccc cctattgacg tcaatgacgg taaatggccc gcctggcatt     840
atgcccagta cgtgacctta tgggactttc ctacttggca gtacatctac gtattagtca     900
tcgctattac catggtgatg cggttttggc agtacatcaa tgggcgtgga tagcggtttg     960
actcacgggg atttccaagt ctccacccca ttgacgtcaa tgggagtttg ttttggcacc    1020
aaaatcaacg ggactttcca aaatgtcgta acaactccgc cccattgacg caaatgggcg    1080
gtaggcgtgt acggtgggag gtctatataa gcagagctct ctggctaact agagaaccca    1140
ctgcttactg gcttatcgaa attaatacga ctcactatag ggagacccaa gctggctagc    1200
accatgacaa acctgcaaga tcaaacccaa cagattgttc cgttcatacg gagccttctg    1260
atgccaacaa ccggaccggc gtccattccg gacgacaccc tggagaagca cactctcagg    1320
tcagagacct cgacctacaa tttgactgtg ggggacacag ggtcagggct aattgtcttt    1380
ttccctggat tccctggctc aattgtgggt gctcactaca cactgcagag caatgggaac    1440
tacaagttcg atcagatgct cctgactgcc cagaacctac cggccagtta caactactgc    1500
aggctagtga gtcggagtct cacagtgagg tcaagcacac tccctggtgg cggcgtttat    1560
gcactaaacg gcaccataaa cgccgtgacc ttccaaggaa gcctgagtga actgacagat    1620
gttagctaca atgggttgat gtctgcaacg gccaacatca acgacaaaat tgggaatgtc    1680
ctggtagggg aggggtcac cgtcctcagc ttacccacat catatgatct tgggtatgtg    1740
aggcttggtg accccattcc tgctataggg cttgacccaa aaatggtagc cacatgtgac    1800
agcagtgaca ggcccagagt ctacaccata actgcagccg atgactacca gttctcatca    1860
cagtaccaac caggtggggt aacaatcaca ctgttctcag ccaacattga tgctatcaca    1920
agcctcagcg ttgggggaga gctcgtgttt caaacaagcg ttcaaggcct tgtactgggc    1980
gccaccatct accttatagg ctttgatggg actacggtaa tcaccagggc tgtggccgca    2040
gacaatgggc tgacggccgg caccgacaat cttatgccat tcaatattgt gattccaacc    2100
aacgagataa cccagccaat tacatccatc aaactggaga tagtgacctc caaaagtggt    2160
ggtcaggcgg gggaccaaat gtcatggtca gcaagtggga gcctagcagt gacgatccac    2220
ggtggcaact atccagggc cctccgtccc gtcacactag tagcctacga aagagtggca    2280
```

```
acaggatccg tcgttacggt cgccggggtg agcaacttcg agctgatccc aaatcctgaa    2340
ctagcaaaga acctggttac agaatacggc cgatttgacc caggagccat gaactacaca    2400
aaattgatac tgagtgagag ggaccgtctt ggcatcaaga ccgtctggcc aacaagggag    2460
tacactgact tccgtgagta cttcatggag gtggccgacc tcaactctcc cctgaagatt    2520
gcaggagcat ttggcttcaa agacataatc cgggccataa ggaggtagtg atctagagat    2580
caagggcgaa ttctgcagat atccatcaca ctggcggccg ctcgagcatg catctagagg    2640
gcccgtttaa acccgctgat cagcctcgac tgtgccttct agttgccagc catctgttgt    2700
ttgcccctcc cccgtgcctt ccttgaccct ggaaggtgcc actcccactg tcctttccta    2760
ataaaatgag gaaattgcat cgcattgtct gagtaggtgt cattctattc tggggggtgg    2820
ggtggggcag gacagcaagg gggaggattg ggaagacaat agcaggcatg ctggggagac    2880
gggaataaat gcaatagcgt tcgagaaaaa tcgttgcaat tagcaacgag ggatatgtta    2940
cccgcccgtg actgtagcag acgttcgagt caataaattt gaaacaaaat ctacaaacct    3000
gcgtatgtgc gatttatttt cggtatacgg gagattggtc aatgcaaggc tcgtaacatt    3060
tacctataga ttcgggtaca tgcaaattcg ttagtgatcc gtcatgcatt tcatattctg    3120
ttccggcatc tgaaatgcat gacgatcac taatatacaa tctcgcctca cgaattgctt    3180
cagcgagaag gtcttccctc gcatccgaga cctcagcagt tccgggaata ttgtttgtat    3240
gcccggcaat tgtgaacgtc gttcgacatc ctggatattc cggctctaag gtaatagtct    3300
ctacgtcatc catgttctgc gagccatcgt ttttctgtac tatttcatca tcggtccttc    3360
gagggcccat ctgttgggac atctgaaaat tatcacacgg ttttgcaagt atacctgatt    3420
gtccataaat tgtaattgtt acgtatatag aatttcccat ccccaaaata gttaagatgc    3480
ctccagaatt attatacacg taggcatcag ttcccatcac ggtacatgta gcgaatggaa    3540
taacacagag cgcttcgggt aatgatgata atgaggctga gtggtgttcg gcggtatatt    3600
cttcaacacg tagtaaataa gagtatataa ttgatccgct g                        3641
```

<210> SEQ ID NO 17
<211> LENGTH: 687
<212> TYPE: DNA
<213> ORGANISM: Cytomegalovirus

<400> SEQUENCE: 17

```
cgatgtacgg gccagatata cgcgttgaca ttgattattg actagttatt aatagtaatc     60
aattacgggg tcattagttc atagcccata tatggagttc cgcgttacat aacttacggt    120
aaatggcccg cctggctgac cgcccaacga ccccccgccca ttgacgtcaa taatgacgta    180
tgttcccata gtaacgccaa tagggacttt ccattgacgt caatgggtgg agtatttacg    240
gtaaactgcc cacttggcag tacatcaagt gtatcatatg ccaagtacgc cccctattga    300
cgtcaatgac ggtaaatggc ccgcctggca ttatgcccag tacgtgacct tatgggactt    360
tcctacttgg cagtacatct acgtattagt catcgctatt accatggtga tgcggttttg    420
gcagtacatc aatgggcgtg atagcggtt tgactcacgg ggatttccaa gtctccaccc    480
cattgacgtc aatgggagtt tgttttggca ccaaaatcaa cgggactttc caaaatgtcg    540
taacaactcc gccccattga cgcaaatggg cggtaggcgt gtacggtggg aggtctatat    600
aagcagagct ctctggctaa ctagagaacc cactgcttac tggcttatcg aaattaatac    660
gactcactat agggagaccc aagctgg                                         687
```

```
<210> SEQ ID NO 18
<211> LENGTH: 244
<212> TYPE: DNA
<213> ORGANISM: Bovine

<400> SEQUENCE: 18
ctagagggcc cgtttaaacc cgctgatcag cctcgactgt gccttctagt tgccagccat      60
ctgttgtttg ccctcccc gtgccttcct tgaccctgga aggtgccact cccactgtcc      120
tttcctaata aaatgaggaa attgcatcgc attgtctgag taggtgtcat tctattctgg      180
ggggtggggt ggggcaggac agcaagggg aggattggga agacaatagc aggcatgctg      240
ggga                                                                   244

<210> SEQ ID NO 19
<211> LENGTH: 4005
<212> TYPE: DNA
<213> ORGANISM: Artificial sequence
<220> FEATURE:
<223> OTHER INFORMATION: Transfer vector

<400> SEQUENCE: 19
tgcatctgtc accaacgcaa agtcggcgtc tacatagaac tttaagattt gtggagcgta      60
gaattatccc atctaacagt tatatacgca catcgggcca cgttccgcct tcgagggcac      120
ttccgacaga tacgaattta agatggatg aataattaaa ttggaaagag taactacatt      180
aatcgagcgt catgacggcg tcccgtgaaa atgggaattt tctactcgaa acaccgtgac      240
atttgacaga cctggaattg ttattctgat atatagtggg tgtgtctggc ggcaacata      300 cataatgtgc atgcgaaacc acttttcag tgtacgctga cattgtgcaa cacggagggg      360
tagcatctac atacaatata tgttgattaa tgattggaga aaaaactatg cagctcgccg      420
atcatatggc taactcgcct tcgtctatat ggcggacccc gcgggaaaaa tcgacgtacc      480
atctgattta caacaccagt aatgaacatg tcgcatccct gcccagatct gtgcgcccat      540
tggcgcgtat cgttgtgaat gccgccgaaa cacttcaggt cggtatgaga gccgggaggc      600
cgccatcagc aggagtttgg cgagaggtgt tgatagaat gatgcacagcc ttccgtgacc      660 acgagcctac tgcgacattt aatgctgcaa atcccattag aaaaatggtc gagacagttc      720
tacagaataa tgaagagccc ccgcggacgc atgctgaaat gggtaatcgc cttatgaaca      780
ttatgtactg gtgttgcttg ggacacgcag gacaatgctc gatatggcag ttgtacgaga      840
cgaatcaggc cattttaagt ttattagatg aagtggttat cggcacaaca aatccctttt      900
gcaccctcga gcaatactgg aagccattat gcaccgcaat cgccaacaag gggacctcat      960
cgcttgttga ggatgccaaa gtggccgagt acctggttag catgcgcaaa ttgatataac      1020
ataggcacgc tctgatgtta cagaccacaa taccgcatac atttattgta aggttgttaa      1080
taaaggttta ttctatgtaa gaccctgcat cgatgtacgg gccagatata cgcgttgaca      1140
ttgattattg actagttatt aatagtaatc aattacgggg tcattagttc atagcccata      1200
tatggagttc cgcgttacat aacttacggt aaatggcccg cctggctgac cgcccaacga      1260
cccccgccca ttgacgtcaa taatgacgta tgttcccata gtaacgccaa tagggacttt      1320
ccattgacgt caatgggtgg actatttacg gtaaactgcc cacttggcag tacatcaagt      1380
gtatcatatg ccaagtacgc cccctattga cgtcaatgac ggtaaatggc ccgcctggca      1440
ttatgcccag tacatgacct tatgggactt tcctacttgg cagtacatct acgtattagt      1500
catcgctatt accatggtga tgcggttttg gcagtacatc aatgggcgtg gatagcggtt      1560
```

```
tgactcacgg ggatttccaa gtctccaccc cattgacgtc aatgggagtt tgttttggca    1620
ccaaaatcaa cgggactttc caaaatgtcg taacaactcc gccccattga cgcaaatggg    1680
cggtaggcgt gtacggtggg aggtctatat aagcagagct ctctggctaa ctagagaacc    1740
cactgcttac tggcttatcg aaattaatac gactcactat agggagaccc aagctggcta    1800
gcgtttaaac ttaagcttgg taccgagctc ggatccacta gtccagtgtg gtggaattct    1860
gcagatatcc agcacagtgg cggccgctcg agtctagagg gcccgtttaa acccgctgat    1920
cagcctcgac tgtgccttct agttgccagc catctgttgt ttgcccctcc cccgtgcctt    1980
ccttgaccct ggaaggtgcc actcccactg tcctttccta taaaatgag gaaattgcat    2040
cgcattgtct gagtaggtgt cattctattc tggggggtgg ggtggggcag gacagcaagg    2100
gggaggattg ggaagacaat agcaggcatg ctggggaatg caggtacaat actttcgaca    2160
ttgcttgtat acatattaaa tactttctca agttcctatt acataaaatg ggatctatca    2220
ttacattcgt taagagtctg gataattta ctgtttgcca gcttcgatct tggaacgtac    2280
tgtggatagt gccttacttg gaatcgtgaa aatttgaaac gtccattatt tggatatctt    2340
ccggttgtcc catatcccgc cctggtaccg ctcggatacc ttgcccgtat ggattcgtat    2400
tgacagtcgc gcaatcgggg accaacaacg cgtgggtcca cactcattcg gaaattttcc    2460
gatgattctg aatatttatt gccgctcgtt acgagtcgtt ggacatatct gtaatacatt    2520
tcttcttctg aaggatcgct gcacatttga tctatacatt ggccaggatg ttcaagtctc    2580
agatgttgca ttctggcaca gcacaacttt atggcatttc cgatgtaatc gtccggcagc    2640
cctgggggag ttctatattc gcatattggg atggtaagga caatagcaga tctcgcaacc    2700
tccaggagg ctataataac gtttttaaag gatggatttc tcataaaaat ctgtcgcaaa    2760
ttacactgag aatatccttt actagcgccg attgagagca tcgtcgtcca attttctaaa    2820
tggaaagaaa acaaggcggg caagagtgtt ccaaacattt tcattttcgg cgaatctctc    2880
aaatcccatg gcgtgcaatt gattgcaaaa ttggcacttc cgttcacgtt tgtatctcca    2940
aactctaaga cacttttaat tgaaaaacta cgttctagtg tggaaagaaa cctataggca    3000
gaccatagaa ctatttgaca ccacatatct ttttgtatgt caaactgacc atgatcgtat    3060
gttgctgaat gcactagggc aattcgctcg cgcgactcca tacattgaat aattccacac    3120
gtcagctcat cggttagcaa ggtccagtag ttgaagtcat ttatttttcc ccgcggctgg    3180
ccaaatctac ctctgggaat atccaagttg tcgaatatga tcgcaccggc tctggtcatg    3240
gtgaaggaac ttgtagcata aagacgcagg tatcataggg gtaatatttt tttattcact    3300
cacatactaa aagtaacgca tattagcacc atgtatgggc tatcaattga catttgcgta    3360
gcactacatc acgattatgt acaacataat gggacaacat atggcaagta gatgcaattt    3420
cctcacacta gttgggttta tctactattg aattttcccc tatctgtgat acacttggga    3480
gcctctacaa gcatattgcc atcatgtacg ttttatcta ctgtcttaac gcccatggga    3540
acggaggcgt cgtcgtcatg tattggacgg caacataggc agcaacacaa attgcgttta    3600
ggtggggtgc atgtggactc gataccaagc ccctgcagct ggggaacgtc tggtggagag    3660
ccgataattt gatatacgca cgccatatta ctgtcgttga agtacgcctt atcttctatg    3720
ttttcaaatt taggttccca agtggacgtg agaagtgttt gtatctcaca tggaatggcc    3780
caaggcattc cagcccaggt gcctggtact ttaatggcaa acaaacgttt tggtagaggt    3840
attgattcta ttgcagttct gcagatatct gcagccccga gtatccacag gctatacgat    3900
acgttatcgg aggcctccga ttctagcatt acatagccgg tcagtagatc ctgccattcg    3960
```

```
gtagcgcaac cggctacatc ttcaaacagt ctcacaataa atgca              4005
```

<210> SEQ ID NO 20
<211> LENGTH: 1731
<212> TYPE: DNA
<213> ORGANISM: Newcastle disease virus

<400> SEQUENCE: 20

```
atggaccgcg ccgttagcca agttgcgtta gagaatgatg aaagagaggc aaaaaataca    60
tggcgcttga tattccggat tgcaatctta ttcttaacag tagtgacctt ggctatatct   120
gtagcctccc ttttatatag catgggggct agcacaccta gcgatcttgt aggcataccg   180
actaggattt ccagggcaga agaaaagatt acatctacac ttggttccaa tcaagatgta   240
gtagatagga tatataagca agtggccctt gagtctccgt tggcattgtt aaatactgag   300
accacaatta tgaacgcaat aacatctctc tcttatcaga ttaatggagc tgcaaacaac   360
agtgggtggg gggcaccaat ccatgaccca gattatatag gggggatagg caaagaactc   420
attgtagatg atgctagtga tgtcacatca ttctatccct ctgcatttca agaacatctg   480
aatttttatcc cggcgcctac tacaggatca ggttgcactc gaatacactc atttgacatg   540
agtgctaccc attactgcta cacccataat gtaatattgt ctggatgcag agatcactca   600
cattcatatc agtatttagc acttggtgtg ctccggacat ctgcaacagg agggtattc   660
ttttctactc tgcgttccat caacctggac gacacccaaa atcggaagtc ttgcagtgtg   720
agtgcaactc ctctggggttg tgatatgctg tgctcgaaag tcacggagac agaggaagaa   780
gattataact cagctgtccc tacgcggatg gtacatggga ggttagggtt cgacggccag   840
taccacgaaa aggacctaga tgtcacaaca ttattcgggg actgggtggc caactaccca   900
ggaataggg gtggatcttt tattgacagc gcgtatggt tctcagtcta cggagggtta   960
aaacccaatt cacccagtga cactgtacag gaagggaaat atgtgatata caagcgatac  1020
aatgacacat gcccagatga gcaagactac cagattcgaa tggccaagtc ttcgtataag  1080
cctggacggt ttggtgggaa cgcatacag caggctatct tatctatcaa ggtgtcaaca  1140
tccttaggcg aagacccggt actgactgta ccgcccaaca cagtcacact catgggggcc  1200
gaaggcagaa ttctcacagt agggacatct catttcttgt atcaacgagg gtcatcatac  1260
ttctctcccg cgttattata tcctatgaca gtcagcaaca aaacagccac tcttcatagt  1320
ccttatacat tcaatgcctt cactcggcca ggtagtatcc cttgccaggc ttcagcaaga  1380
tgccccaact cgtgtgttac tggagtctat acagatccat atcccctaat cttctataga  1440
aaccacacct tgcgaggggt attcgggaca atgcttgatg gtgtacaagc aagacttaac  1500
cctgcgtctg cagtattcga tagcacatcc cgcagtcgca ttactcgagt gagttcaagc  1560
agaaccaaag cagcatacac aacatcaact tgttttaaag tggtcaagac taataagacc  1620
tattgtctca gcattgctga aatatctaat actctcttcg gagaattcag aatcgtcccg  1680
ttactagttg agatcctcaa agatgacggg gttagagaag ccaggtctgg c            1731
```

<210> SEQ ID NO 21
<211> LENGTH: 3471
<212> TYPE: DNA
<213> ORGANISM: Newcastle disease virus

<400> SEQUENCE: 21

```
atgggctcca gaccttctac caagaaccca gcacctatga tgctgactat ccggggttgcg    60
```

```
ctggtactga gttgcatctg tccggcaaac tccattgatg gcaggcctct tgcagctgca      120
ggaattgtgg ttacaggaga caaagccgtc aacatataca cctcatccca gacaggatca      180
atcatagtta agctcctccc gaatctgccc aaggataagg aggcatgtgc gaaagccccc      240
ttggatgcat acaacaggac attgaccact ttgctcaccc cccttggtga ctctatccgt      300
aggatacaag agtctgtgac tacatctgga ggggggagac aggggcgcct tataggcgcc      360
attattggcg gtgtggctct tggggttgca actgccgcac aaataacagc ggccgcagct      420
ctgatacaag ccaaacaaaa tgctgccaac atcctccgac ttaaagagag cattgccgca      480
accaatgagg ctgtgcatga ggtcactgac ggattatcgc aactagcagt ggcagttggg      540
aagatgcagc agtttgttaa tgaccaattt aataaaacag ctcaggaatt agactgcatc      600
aaaattgcac agcaagttgg tgtagagctc aacctgtacc taaccgaatt gactacagta      660
ttcggaccac aaatcacttc acctgcttta aacaagctga ctattcaggc actttacaat      720
ctagctggtg aaatatgga ttacttattg actaagttag gtgtagggaa caatcaactc       780
agctcattaa tcggtagcgg cttaatcacc ggtaaccctaA ttctatacga ctcacagact      840
caactcttgg gtatacaggt aactctacct tcagtcggga acctaaataa tatgcgtgcc      900
acctacttgg aaaccttatc cgtaagcaca accagggggt tgcctcggc acttgtccca       960
aaagtggtga cacaggtcgg ttctgtgata aagaacttg acacctcata ctgtatagaa      1020
actgacttag atttatattg tacaagaata gtaacgttcc ctatgtcccc tggtattta       1080
tcctgcttga gcggcaatac gtcggcctgt atgtactcaa agaccgaagg cgcacttact     1140
acaccataca tgactatcaa aggttcagtc atcgccaact gcaagatgac aacatgtaga     1200
tgtgtaaacc ccccgggtat catatcgcaa actatggag aagccgtgtc tctaatagat       1260
aaacaatcat gcaatgtttt atccttaggc gggataactt taaggctcag tgggaattc      1320
gatgtaactt atcagaagaa tatctcaata caagattctc aagtaataat aacaggcaat      1380
cttgatatct caactgagct tgggaatgtc aacaactcga tcagtaatgc tttgaataag      1440
ttagaggaaa gcaacagaaa actagacaaa gtcaatgtca aactgactag cacatctgct     1500
ctcattacct atatcgtttt gactatcata tctcttgttt ttggtatact agcctgatt      1560
ctagcatgct acctaatgta caagcaaaag gcgcaacaaa agaccttatt atggcttggg     1620
aataatactc tcgatcagat gagagccact acaaaaatgg gaagcggagc tactaacttc     1680
agcctgctga agcaggctgg agacgtggag gagaaccctg gacctggaag cggatctaga    1740
atggaccgcg ccgttagcca agttgcgtta gagaatgatg aaagagaggc aaaaaataca    1800
tggcgcttga tattccggat tgcaatctta ttcttaacag tagtgacctt ggctatatct    1860
gtagcctccc ttttatatag catgggggct agcacaccta gcgatcttgt aggcataccg     1920
actaggattt ccagggcaga agaaaagatt acatctacac ttggttccaa tcaagatgta    1980
gtagataga tatataagca agtggccctt gagtctccgt tggcattgtt aaatactgag      2040
accacaatta tgaacgcaat aacatctctc tcttatcaga ttaatggagc tgcaaacaac    2100
agtgggtggg gggcaccaat ccatgaccca gattatatag gggggatagg caaagaactc    2160
attgtagatg atgctagtga tgtcacatca ttctatccct ctgcatttca agaacatctg    2220
aattttatcc cggcgcctac tacaggatca ggttgcactc gaatacctc atttgacatg    2280
agtgctaccc attactgcta cacccataat gtaatattgt ctggatgcag agatcactca    2340
cattcatatc agtatttagc acttggtgtg ctccggacat ctgcaacagg gagggtattc    2400
ttttctactc tgcgttccat caacctggac gacacccaaa atcggaagtc ttgcagtgtg    2460
```

```
agtgcaactc ctctgggttg tgatatgctg tgctcgaaag tcacggagac agaggaagaa    2520
gattataact cagctgtccc tacgcggatg gtacatggga ggttagggtt cgacggccag    2580
taccacgaaa aggacctaga tgtcacaaca ttattcgggg actgggtggc caactaccca    2640
ggaatagggg gtggatcttt tattgacagc cgcgtatggt tctcagtcta cggagggtta    2700
aaacccaatt cacccagtga cactgtacag gaagggaaat atgtgatata caagcgatac    2760
aatgacacat gcccagatga gcaagactac cagattcgaa tggccaagtc ttcgtataag    2820
cctggacggt ttggtgggaa acgcatacag caggctatct tatctatcaa ggtgtcaaca    2880
tccttaggcg aagacccggt actgactgta ccgcccaaca cagtcacact catggggcc     2940 gaaggcagaa ttctcacagt agggacatct catttcttgt atcaacgagg gtcatcatac    3000
ttctctcccg cgttattata tcctatgaca gtcagcaaca aaacagccac tcttcatagt    3060
ccttatacat tcaatgcctt cactcggcca ggtagtatcc cttgccaggc ttcagcaaga    3120
tgccccaact cgtgtgttac tggagtctat acagatccat atccctaat cttctataga    3180 aaccacacct tgcgagggt attcgggaca atgcttgatg gtgtacaagc aagacttaac    3240
cctgcgtctg cagtattcga tagcacatcc cgcagtcgca ttactcgagt gagttcaagc    3300
agaaccaaag cagcatacac aacatcaact tgttttaaag tggtcaagac taataagacc    3360
tattgtctca gcattgctga aatatctaat actctcttcg gagaattcag aatcgtcccg    3420
ttactagttg agatcctcaa agatgacggg gttagagaag ccaggtctgg c             3471

<210> SEQ ID NO 22
<211> LENGTH: 1659
<212> TYPE: DNA
<213> ORGANISM: Newcastle disease virus

<400> SEQUENCE: 22
atgggctcca gaccttctac caagaaccca gcacctatga tgctgactat ccgggttgcg      60
ctggtactga gttgcatctg tccggcaaac tccattgatg gcaggcctct tgcagctgca     120
ggaattgtgg ttacaggaga caaagccgtc aacatataca cctcatccca gacaggatca     180
atcatagtta agctcctccc gaatctgccc aaggataagg aggcatgtgc gaaagccccc     240
ttggatgcat acaacaggac attgaccact ttgctcaccc cccttggtga ctctatccgt     300
aggatacaag agtctgtgac tacatctgga ggggggagac aggggcgcct tataggcgcc     360
attattggcg gtgtggctct tggggttgca actgccgcac aaataacagc ggccgcagct     420
ctgatacaag ccaaacaaaa tgctgccaac atcctccgac ttaaagagag cattgccgca     480
accaatgagg ctgtgcatga ggtcactgac ggattatcgc aactagcagt ggcagttggg     540
aagatgcagc agtttgttaa tgaccaattt aataaaacag ctcaggaatt agactgcatc     600
aaaattgcac agcaagttgg tgtagagctc aacctgtacc taaccgaatt gactacagta    660
ttcggaccac aaatcacttc acctgccttta aacaagctga ctattcaggc actttacaat    720
ctagctggtg gaaatatgga ttacttattg actaagttag gtgtagggaa caatcaactc    780
agctcattaa tcggtagcgg cttaatcacc ggtaacccta ttctatacga ctcacagact    840
caactcttgg gtatacaggt aactctacct tcagtcggga acctaaataa tatgcgtgcc    900
acctacttgg aaaccttatc cgtaagcaca accaggggat tgcctcggc acttgtccca    960 aaagtggtga cacaggtcgg ttctgtgata gaagaacttg acacctcata ctgtatagaa   1020
actgacttag atttatattg tacaagaata gtaacgttcc ctatgtcccc tggtatttat   1080
```

```
tcctgcttga gcggcaatac gtcggcctgt atgtactcaa agaccgaagg cgcacttact    1140
acaccataca tgactatcaa aggttcagtc atcgccaact gcaagatgac aacatgtaga    1200
tgtgtaaacc ccccgggtat catatcgcaa aactatggag aagccgtgtc tctaatagat    1260
aaacaatcat gcaatgtttt atccttaggc gggataactt taaggctcag tggggaattc    1320
gatgtaactt atcagaagaa tatctcaata caagattctc aagtaataat aacaggcaat    1380
cttgatatct caactgagct tgggaatgtc aacaactcga tcagtaatgc tttgaataag    1440
ttagaggaaa gcaacagaaa actagacaaa gtcaatgtca aactgactag cacatctgct    1500
ctcattacct atatcgtttt gactatcata tctcttgttt ttggtatact tagcctgatt    1560
ctagcatgct acctaatgta caagcaaaag gcgcaacaaa agaccttatt atggcttggg    1620
aataatactc tcgatcagat gagagccact acaaaaatg                          1659
```

RECOMBINANT TURKEY HERPESVIRUS VACCINES AND USES THEREOF

CROSS-REFERENCE TO RELATED APPLICATIONS

This application claims the benefit of U.S. Provisional Application No. 62/203,305, filed Aug. 10, 2015, herein incorporated by reference in its entirety.

FIELD OF THE INVENTION

The present invention relates to the field of immunology and more specifically to methods and compositions for producing vector vaccines for treatment of diseases in poultry.

INCORPORATION OF SEQUENCE LISTING

The sequence listing that is contained in the file named "TAMC039US_ST25.txt," which is 28.6 kilobytes as measured in Microsoft Windows operating system and was created on Aug. 2, 2016, is filed electronically herewith and incorporated herein by reference.

BACKGROUND OF THE INVENTION

Vaccination of poultry is a widely used strategy to prevent outbreaks of Marek's disease (MD), infectious bursal disease (IBD), Newcastle disease (ND), infectious bronchitis (IB), avian influenza (AI), and infectious laryngotracheitis (ILT). Live vaccines are currently used to control these diseases. Using live vaccines has the disadvantage of protecting against only a single disease and many live vaccines used in the poultry industry cause a mild form of the disease affecting production yields. Simultaneous protection of poultry against multiple diseases through the use of a single vaccine would be beneficial. In recent years, recombinant avian viral vectors have been used experimentally and commercially to vaccinate poultry against these diseases. The serotype 3 Marek's disease virus herpesvirus of turkey (HVT) is the most commonly used backbone vector in the poultry industry. HVT is also the most commonly used vaccine to control MD. Currently there are HVT-vectored IBD, HVT-vectored ND, HVT-vectored AT, and HVT-vectored ILT vaccines used to control disease in poultry flocks around the world.

SUMMARY OF THE INVENTION

In one aspect, the invention provides a recombinant viral vector comprising at least one transgene inserted into a Marek's disease viral genome in a region selected from the group consisting of: (a) an intergenic region flanked by HVT10 (UL3) and HVT11 (UL4) in the unique long region of the genome; and (b) an intergenic region flanked by HVT86 (US10) and HVT87 (Sorf3) in the unique short region of the genome. In another embodiment, the at least one transgene comprises a first transgene inserted into the intergenic region flanked by HVT10 (UL3) and HVT11 (UL4) in the unique long region of the genome, and a second transgene inserted into the intergenic region flanked by HVT86 (US10) and HVT87 (Sorf3) in the unique short region of the genome, or the at least one transgene comprises more than one transgene inserted in both the intergenic region flanked by HVT10 (UL3) and HVT11 (UL4) in the unique long region of the genome, and the intergenic region flanked by HVT86 (US10) and HVT87 (Sorf3) in the unique short region of the genome. In another embodiment, the antigenic viral gene comprises a gene selected from the group consisting of an infectious bursal disease virus gene, a Newcastle disease virus gene, an avian influenza virus gene, and an infectious laryngotracheitis virus gene. In another embodiment, the infectious bursal disease virus gene is a VP2 gene, or the Newcastle disease virus gene is an F gene or an HN gene or an F/HN chimera. In another embodiment, the at least one transgene is operatively linked to a heterologous promoter, such as a promoter selected from the group consisting of a human cytomegalovirus IE promoter, a guinea pig CMV promoter, an SV40 promoter, a Pseudorabies Virus promoter, a glycoprotein X promoter, a Herpes Simplex Virus-1 promoter, and a Marek's disease viruses promoters. In another embodiment, the at least one transgene is operatively linked to a polyA signal, such as a bovine growth hormone polyA signal, an SV40 polyA signal, an AcNPV 1629 ORF poly(A) signal, and an HSV TK polyA signal. In still further embodiments, the at least one transgene is inserted into a Marek's disease viral genome in an intergenic region flanked by HVT10 (UL3) and HVT11 (UL4) in the unique long region of the genome.

In other embodiments, the invention provides an immunogenic composition comprising such a recombinant viral vector. In an embodiment, the at least one transgene comprises a first transgene inserted into the viral genome in an intergenic region flanked by HVT10 (UL3) and HVT11 (UL4) in the unique long region of the genome; and a second transgene inserted into the viral genome in an intergenic region flanked by HVT86 (US10) and HVT87 (Sorf3) in the unique short region of the genome. In another embodiment, such an immunogenic composition further comprises at least a third transgene conferring protection against a third disease. In still further embodiments, the at least one transgene is operatively linked to a heterologous promoter, or the first and second transgenes are operatively linked to the same promoter, or the first transgene is operatively linked to a heterologous promoter and the second transgene is operatively linked to a second heterologous promoter. In further embodiments, the at least one transgene encodes a viral gene selected from the group consisting of an infectious bursal disease virus gene, a Newcastle disease virus gene, an avian influenza virus gene, and an infectious laryngotracheitis virus gene, or the infectious bursal disease virus gene is a VP2 gene, or the Newcastle disease virus gene is an F gene or an HN gene or an F/HN chimera.

In another aspect, the invention provides a method for preventing or inhibiting Marek's disease in combination with at least a second disease in poultry, comprising providing a composition as described herein to a bird, wherein the composition is provided in an amount effective to prevent or inhibit Marek's disease and the at least a second disease in the bird. In one embodiment, the composition is provided to the bird by injection. In other embodiments, the injection is selected from the group consisting of intravenous injection, intramuscular injection, subcutaneous injection, and in ovo injection, or the composition is provided to the bird prior to infection with or exposure to a disease. In another embodiment, the bird is a species of poultry, such as a chicken, a turkey, a quail, a goose, a duck, a swan, a guinea, and a pigeon. In a still further embodiment, the composition is provided to the bird in combination with a non-naturally occurring pharmaceutically acceptable carrier.

BRIEF DESCRIPTION OF THE DRAWINGS

FIG. 1—Shows the orientation of the cloned VP2 gene in the pCR Topo TA cloning vector.

FIG. 2—Shows the cloned VP2 gene in the pcDNA3.1 cloning vector after digestion with NheI and XbaI.

FIG. 3—Shows the pcDNA VP2 E/2512 construct in which the corresponding fragment of the Edgar VP2 gene was removed.

FIG. 4—Shows an amplified HVT DNA fragment corresponding to positions 12878-14149 of the HVT genome in the pCR 2.1 Topo TA vector. The left arm of the amplified HVT DNA segment was approximately 507 bp, and the right arm was 765 bp for homologous recombination.

FIG. 5—Top panel shows the construct produced from insertion of the VP2 E/2512 gene cassette into the HincII (13385-13386) site of the pCR Topo TA HVT 12878-14149. Bottom panel shows elements of the VP2 E/2512 expression cassette, including the human cytomegalovirus (CMV) promoter and bovine growth hormone polyA signal.

BRIEF DESCRIPTION OF THE SEQUENCES

SEQ ID NO:1—IBDV VP2 Start NheI primer for amplification of VP2 gene from Edgar strain of infectious bursal disease virus (IBDV) along with SEQ ID NO:2.

SEQ ID NO:2—IBDV VP2 end XbaI primer for amplification of VP2 gene from Edgar strain of IBDV along with SEQ ID NO: 1.

SEQ ID NO:3—HVT>12878 primer for amplification of a DNA fragment corresponding to 12878-14149 of the HVT genome along with SEQ ID NO:4.

SEQ ID NO:4—HVT<14149 primer for amplification of a DNA fragment corresponding to 12878-14149 of the HVT genome along with SEQ ID NO:3.

SEQ ID NO:5—pCVM primer for amplification of the VP2 E/2512 expression cassette, and for amplification of regulatory sequences corresponding to the cytomegalovirus immediate early (IE) promoter and the bovine growth hormone polyA region, along with SEQ ID NO:6.

SEQ ID NO:6—BGH pA primer for amplification of the VP2 E/2512 expression cassette, and for amplification of regulatory sequences corresponding to the cytomegalovirus immediate early (IE) promoter and the bovine growth hormone polyA region, along with SEQ ID NO:5.

SEQ ID NO:7—rVP2>628 primer for detection of VP2 gene in HVT-E2512 recombinant, along with SEQ ID NO:8, generating a 360-bp DNA fragment.

SEQ ID NO:8—rVP2<988 primer for detection of VP2 gene in HVT-E2512 recombinant, along with SEQ ID NO:7, generating a 360-bp DNA fragment.

SEQ ID NO:9—NDV F>start NheI primer for amplification of the F gene from the Lasota strain of Newcastle disease virus along with SEQ ID NO:10; and for cloning of the F-P2A-HN gene from the Lasota strain of Newcastle disease virus along with SEQ ID NO:13.

SEQ ID NO:10—NDV F>end XbaI primer for amplification of the F gene from the Lasota strain of Newcastle disease virus.

SEQ ID NO:11—NDV HN start>XbaI primer for cloning of the HN gene from the Lasota strain of Newcastle disease virus.

SEQ ID NO:12—NDV HN end<XbaI primer for cloning of the HN gene from the Lasota strain of Newcastle disease virus.

SEQ ID NO:13—NDV F-P2A end<Xba primer for cloning of the F-P2A-HN gene Lasota strain of Newcastle disease.

SEQ ID NO:14—Nucleotide sequence of the VP2 E2512 open reading frame.

SEQ ID NO:15—Deduced amino acid sequence of the VP2 E2512 open reading frame.

SEQ ID NO:16—Sequence of the HVT transfer vector containing HVT genomic DNA, the human cytomegalovirus (CMV) promoter, the VP2 E2512 open reading frame, and the bovine growth hormone polyadenylation signal.

SEQ ID NO:17—Sequence of cytomegalovirus (CMV) enhancer-promoter region of the HVT transfer vector.

SEQ ID NO:18—Sequence of the bovine growth hormone polyadenylation signal.

SEQ ID NO:19—Sequence of the HVT US10-Sorf3 transfer vector.

SEQ ID NO:20—Sequence of the HN gene from the Lasota strain of the Newcastle disease virus that was cloned into the US10/Sorf3 site.

SEQ ID NO:21—Sequence of the open reading frames of the F-2A-HN gene chimera from the Lasota strain of the Newcastle disease virus that was cloned into the US10/Sorf3 site.

SEQ ID NO:22—Sequence of the F gene from the Lasota strain of the Newcastle disease virus that was cloned into the US10/Sorf3 site.

DETAILED DESCRIPTION

The following is a detailed description provided to aid those skilled in the art. Those of ordinary skill in the art may make modifications and variations in the embodiments described herein without departing from the spirit or scope of the present invention.

The present invention provides a recombinant Marek's disease virus comprising at least one transgene inserted into the viral genome in a region selected from the group consisting of: (a) an intergenic region flanked by HVT10 (UL3) and HVT11 (UL4) in the unique long region of the genome; and (b) an intergenic region flanked by HVT86 (US10) and HVT87 (Sorf3) in the unique short region of the genome. Also provided are immunogenic compositions and methods for treating or preventing Marek's disease (MD) in combination with at least a second viral disease.

Marek's disease is a common lymphoproliferative disease of chickens, caused by Marek's disease virus (MDV), which can result in significant losses in the poultry industry. Currently, MD is controlled in poultry using vaccines using serotype 3 of MDV, which is the related Herpesvirus of Turkeys (HVT). By introducing genes from poultry viruses other than MDV into the HVT genome at particular genetic positions, the inventors have been able to develop novel recombinant viral vaccines that enable simultaneous protection in poultry against MD and one or more additional diseases through administration of a single viral vaccine.

In accordance with the invention, recombinant viral vectors as described herein may enable protection of poultry against two or more different viral pathogens by providing recombinant viral vectors that express genes from such viral pathogens. In some embodiments, the recombinant viral vectors of the present invention may be provided to poultry in an immunogenic composition as described herein. Genes from any viral pathogen suitable for use with a recombinant viral vector as described herein may be used. For example, in some embodiments, the recombinant viral vector may express genes from Newcastle disease Virus (NDV), infectious bursal disease virus (IBDV), avian influenza virus (AIV), infectious bronchitis (IBV), and infectious laryngotracheitis (ILTV) or the like.

In accordance with the invention, a transgene conferring protection from or resistance to a particular virus or viruses may be inserted into the viral genome at a specific location. For example, in some embodiments, a transgene as described herein may be inserted into the viral genome in an intergenic region flanked by HVT10 (UL3) and HVT11 (UL4) in the unique long region of the genome, and/or may be inserted in an intergenic region flanked by HVT86 (US10) and HVT87 (Sorf3) in the unique short region of the genome. In another embodiment, a recombinant Marek's disease virus of the invention may have a transgene inserted in both of these regions. In other embodiments, more than one transgene may be inserted into one or both of these regions.

In some embodiments, the recombinant viral vector may express multiple genes from a single virus species or may express genes from more than one virus species in order to obtain resistance to multiple viruses. For instance, in one embodiment, the invention provides a recombinant viral vector comprising the HVT genome and at least one transgene from a different viral pathogen, thus providing protection in a bird such as poultry against Marek's disease, and at least one other viral disease. For example, in one embodiment, a recombinant viral vector in accordance with the invention may provide protection in poultry against MDV and NDV, or may provide protection against MDV and IBDV, or may provide protection against MDV, NDV, and IBDV.

Viral antigens for expression in poultry by a recombinant viral vector of the present invention may be encoded by a viral gene, such as a viral gene as described herein. One of skill in the art will appreciate in this regard that it may not be required to incorporate the entirety of a particular viral gene in order to obtain a desired viral resistance. Rather, a portion of such a gene may be used. It may be desirable to choose a particular portion of a desired gene that is specific to any given targeted virus or viruses. Optimization of a desired viral protein or sequence encoding such a protein regardless of the length of the protein may be readily carried out using the methodologies known in the art that are appropriate for use with the present invention. One of skill in the art will appreciate that modifications may be made to a viral gene or genes, or the proteins encoded thereby, to increase the activity of the viral protein when introduced into the subject. Modifications made to viral genes or proteins may increase or decrease the response in a host to a specific virus.

In certain embodiments, a recombinant Marek's disease virus or recombinant viral vector of the invention may have a transgene encoding an IBDV viral protein or gene product, such as an IBDV VP2 protein or gene product. In another embodiment, such a recombinant virus or viral vector may have a transgene encoding a NDV viral protein or gene product, such as a NDV F or HN protein or gene product. In another embodiment, such a recombinant virus or viral vector may have a transgene encoding an Avian Influenza Virus (AIV) viral protein or gene product, such as a AIV HA or N protein or gene product. In another embodiment, such a recombinant virus or viral vector may have a transgene encoding an Infectious Laryngotracheitis Virus (ILTV) viral protein or gene product, such as a ILTV gB or gC or gD or gE or gI, UL-32 protein or gene product. In another embodiment, such a recombinant virus or viral vector may have a transgene encoding an Infectious Bronchitis Virus (IBV) viral protein or gene product, such as IBV S1 or S2 protein or gene product. A transgene of the invention may have more than one gene, including a gene-fusion protein or gene product, such a NDV F-HN fusion protein, chimera, or gene product. In some embodiments, the complete coding sequence of such a gene may be used such that a full-length or fully functional protein or polypeptide is produced. Alternatively, a portion or fragment of a viral protein or polypeptide may be sufficient to provide protection from or resistance to a particular virus or viruses.

Isolation of Viral Genes or Proteins

In embodiments of the invention, a viral gene as described herein may be isolated using nucleic acid probes and/or oligonucleotides under stringent hybridization conditions, PCR or microarray, screening DNA libraries, or using any other methods known in the art. One of skill in the art will readily understand how to isolate viral genes or proteins for use according to the invention. Alternatively, expression libraries may be used to clone a virus, polymorphic variants thereof, orthologs, or alleles by detecting homologs immunologically with antisera or purified antibodies directed against a virus from another species or portions thereof.

Methods for making and screening cDNA libraries are well known in the art. For example, to make a cDNA library to clone viral genes expressed by the genome, mRNA may be reverse-transcribed into cDNA using reverse transcriptase. The cDNA may then be ligated into a vector, such as recombinant vector, and introduced into a host cell or organism for propagation, screening, and cloning.

For a genomic library, DNA may be extracted from a desired tissue and may be digested using biological enzymes, or may be mechanically sheared. The resulting DNA fragments may then be isolated from undesired DNA fragments and constructed into an appropriate vector, which may then be packaged in vitro. Recombinant vectors may be analyzed by any method known in the art.

Methods such as polymerase chain reaction (PCR and RT-PCR) and ligase chain reaction (LCR) may be used to amplify nucleic acid sequences directly from mRNA, from cDNA, from genomic libraries or cDNA libraries. Degenerate oligonucleotides can be designed to amplify homologs using the sequences provided herein. Restriction endonuclease sites may be incorporated into the primers. Polymerase chain reaction or other in vitro amplification methods may also be useful, for example, to clone nucleic acid sequences that code for proteins to be expressed, to make nucleic acids to use as probes for detecting the presence of the disease to be targeted, such as MDV, NDV, and/or IBDV, encoding mRNA in biological samples, for nucleic acid sequencing, or for other purposes. Genes amplified by PCR may be purified from agarose and cloned into an appropriate vector.

Expression of viral genes may also be analyzed by techniques known in the art, e.g., reverse transcription and amplification of mRNA, isolation of total RNA or polyA RNA, northern blotting, dot blotting, in situ hybridization, RNase protection, high density polynucleotide array technology, and the like.

Nucleic acids encoding a viral genome or protein may be used with high density oligonucleotide array technology (e.g., GeneChip™) to identify viral genes, orthologs, alleles, variants thereof, and polymorphic variants in this invention. The gene of choice may be cloned into an intermediate vector before transformation into prokaryotic or eukaryotic cells for replication and/or expression. These intermediate vectors may be prokaryote vectors, e.g., plasmids, or shuttle vectors.

Modification of Nucleic Acids

Any number of methods well known to those skilled in the art can be used to isolate and manipulate a DNA molecule. For example, polymerase chain reaction (PCR) technology may be used to amplify a particular starting DNA molecule and/or to produce variants of the starting DNA molecule. DNA molecules, or fragments thereof, can also be obtained by any techniques known in the art, including directly synthesizing a fragment by chemical means. Thus, all or a portion of a nucleic acid as described herein may be synthesized.

As used herein, the term "complementary nucleic acids" refers to two nucleic acid molecules that are capable of specifically hybridizing to one another, wherein the two molecules are capable of forming an anti-parallel, double-stranded nucleic acid structure. In this regard, a nucleic acid molecule is said to be the complement of another nucleic acid molecule if they exhibit complete complementarity. Two molecules are said to be "minimally complementary" if they can hybridize to one another with sufficient stability to permit them to remain annealed to one another under at least conventional low-stringency conditions. Similarly, the molecules are said to be complementary if they can hybridize to one another with sufficient stability to permit them to remain annealed to one another under conventional high-stringency conditions. Conventional stringency conditions are described by Sambrook, et al. (1989), and by Haymes et al. (1985).

Departures from complete complementarity are permissible, as long as the capacity of the molecules to form a double-stranded structure remains. Thus, in order for a nucleic acid molecule or a fragment of the nucleic acid molecule to serve as a primer or probe such a molecule or fragment need only be sufficiently complementary in sequence to be able to form a stable double-stranded structure under the particular solvent and salt concentrations employed.

As used herein, the terms "sequence identity," "sequence similarity," or "homology" are used to describe sequence relationships between two or more nucleotide sequences. The percentage of "sequence identity" between two sequences is determined by comparing two optimally aligned sequences over a specific number of nucleotides, wherein the portion of the sequence in the comparison window may comprise additions or deletions (i.e., gaps) as compared to a reference sequence. Two sequences are said to be identical if nucleotide at every position is the same. A nucleotide sequence when observed in the 5' to 3' direction is said to be a "complement" of, or complementary to, a second nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is complementary to a reference nucleotide sequence will exhibit a sequence identical to the reverse complement sequence of the reference nucleotide sequence.

Recombinant Vectors and Host Cells

A recombinant DNA vector may be, for example, a linear or circular plasmid. The vector system may be a single vector or plasmid or two or more vectors or plasmids that together contain the total DNA to be introduced into the genome of a host cell. A recombinant vector as described herein may be an expression vector, for example to enable production of a desired protein in a host cell such as a bacterial cell. Nucleic acid molecules as described herein, or complements or fragments thereof, may be inserted into a vector under the control of a suitable promoter that functions in one or more microbial hosts to drive expression of a linked coding sequence or other DNA sequence. Many vectors are available and known in the art for this purpose, and selection of the appropriate vector depends on the size of the nucleic acid to be inserted into the vector and the host cell to be transformed with the vector. Each vector may contain various components depending on its function (e.g. amplification of DNA or expression of DNA) and the particular host cell with which it is compatible. Vector components for bacterial transformation generally include, but are not limited to, one or more of the following: a signal sequence, an origin of replication, one or more selectable marker genes, and an inducible promoter allowing the expression of exogenous DNA.

As used herein, a "recombinant Marek's disease virus" or "recombinant HVT" or "recombinant virus" denotes an infective virus or viral particle that has been genetically modified by the incorporation into the viral genome of one or more heterologous nucleic acid sequences, i.e. DNA coding for a viral gene or fragment or portion thereof not identical to the nucleic acid sequence of a gene naturally present in the virus. On infection of a cell by the recombinant Marek's disease virus, the recombinant virus expresses the heterologous gene in the form of a heterologous polypeptide.

A "recombinant viral vector" or "viral vector" as used herein refers to a recombinant construct that is inserted into a virus for introduction into a host cell. Such a vector according to the invention may be derived from any HVT strain. As appropriate, viral genes or protein-coding sequences may be incorporated into such a recombinant viral vector as described herein for introduction into a chicken or other poultry for protection from one or more viral diseases.

As used herein, an "insertion site" refers to a region in a viral genome into which a transgene or exogenous DNA is inserted. The insertion sites of the present invention may be intergenic regions. An intergenic region in accordance with the invention may be flanked by HVT10 (UL3) and HVT11 (UL4) in the unique long region of the genome or may be flanked by HVT86 (US10) and HVT87 (Sorf3) in the unique short region of the genome. In some embodiments, the insertion sites of the present invention may include all or a portion of a flanking gene on either side of the intergenic region. Insertion of one or more transgenes into one of these regions enables the production of a recombinant viral vector that can then be introduced into a chicken or other poultry for protection against one or more diseases. In some embodiments, a transgene as described herein may be inserted at an insertion site as disclosed herein in addition to one or more insertion sites known in the art, for example including, but not limited to the IG1 locus of the HVT genome, the SORF3-US2 locus of the HVT genome, a locus between the HVT 65 and HVT 66 genes, and a site described in U.S. Pat. Nos. 6,045,803 and 5,980,906, incorporated herein by reference in their entireties.

As used herein, the term "operably linked" when used in reference to a regulatory sequence and a nucleotide sequence, means that the regulatory sequence causes regulated expression of the linked structural nucleotide sequence. The terms "regulatory sequences," "regulatory elements," or "control elements" refer to nucleotide sequences located upstream (5' sequences), within, or downstream (3' sequences) of a structural nucleotide sequence. Such sequences influence the timing and level or amount of transcription, RNA processing or stability, or translation of an associated structural nucleotide sequence. Regulatory sequences may include but are not limited to promoters, leader sequences, introns, enhancers, stem-loop structures, repressor binding sequences, and polyadenylation recognition sequences, including, but not limited to, a bovine growth hormone polyA signal, a Simian virus 40 (SV40) polyA signal, an *Autographa californica* nuclear polyhedrosis virus (AcNPV) 1629 ORF poly(A) signal, and a herpes simplex virus (HSV) thymidine kinase (TK) polyA signal. One of skill in the art will recognize that different combinations of promoters and/or regulatory elements may be used to increase or decrease expression of a transgene as described herein.

Promoters that function in different species are also well known in the art. Promoters useful for expression of polypeptides include those that are inducible, viral, synthetic, or constitutive, and/or promoters that are tissue-specific, temporally regulated, spatially regulated, and spatio-temporally regulated. For example, a promoters useful in accordance with the invention may include, but is not limited to, an immediate early (IE) cytomegalovirus (CMV) promoter, guinea pig CMV promoter, an SV40 promoter, Pseudorabies Virus promoters such as that of glycoprotein X promoter, Herpes Simplex Virus-1, such as the alpha 4 promoter, Marek's disease viruses promoters, including any isolate or strain of MDV, such as MDV-1, MDV-2, and HVT, for example a promoter controlling expression of glycoproteins such as gC, gB, gE, or gI, Infectious Laryngotracheitis Virus promoters such as those of glycoprotein gB, gE, gI, gD genes, or any other suitable promoters. One of skill in the art would be well aware of how to identify a promoter useful in accordance with the invention.

In accordance with the invention, a recombinant Marek's disease virus or recombinant viral vector as described herein may comprise one or more transgenes operatively linked to one or more promoters for expression of one or more viral proteins or peptides or fragments or portions thereof. In some embodiments, a single transgene may be operatively linked to a single promoter, or more than one transgene may be operatively linked to a single promoter. In other embodiments, more than one transgene may be present in a recombinant vector wherein a first transgene is operatively linked to a first promoter, a second transgene is operatively linked to a second promoter.

Construction and Selection of Vectors

Construction of vectors containing one or more components as described herein useful for inserting genes or transgenes, or portions thereof, into a target site is known to one of skill in the art and may employ standard recombinant DNA techniques. A recombinant DNA vector or construct may comprise a selectable marker that confers a selectable phenotype to a cell. Selectable markers may also be used to select for cells that contain the exogenous nucleic acids encoding polypeptides or proteins as described herein. Such a marker may encode for example, biocide resistance, or antibiotic resistance (e.g., kanamycin, G418, bleomycin, hygromycin, etc.). Selectable markers are well known to one of skill in the art and may include any markers suitable for use in accordance with the invention.

A recombinant vector or construct may also include a screenable marker, which may be used to monitor expression but which may not result in death of a cell. Suitable screenable markers may include for example, a β-glucuronidase or uidA gene (GUS), one or more of the various fluorescent protein genes, such as green fluorescent protein (GFP), red fluorescent protein (RFP), or any one of a large family of proteins which fluoresce at characteristic wavelengths, a β-lactamase gene, a gene that encodes an enzyme for which various chromogenic substrates are known, a luciferase gene, a xylE gene, which encodes a catechol dioxygenase that converts chromogenic catechols, an α-amylase gene, a tyrosinase gene, which encodes an enzyme capable of oxidizing tyrosine to DOPA and dopaquinone, which in turn condense to melanin, or an α-galactosidase, which catalyzes a chromogenic α-galactose substrate.

Expression of Proteins in Host Cells

To obtain high level expression of a cloned viral gene as described herein, a nucleic acid may be subcloned into an expression vector that contains a strong promoter to direct transcription, and a transcription/translation terminator. For encoded proteins, a ribosome binding site for translation initiation may also be included. Suitable promoters for use in expression vectors are well known in the art, such as a bacterial promoter, a viral promoter, or the like. Expression systems for expressing a protein are available in a number of prokaryotic and eukaryotic species known in the art. Commercial kits for such expression systems are also readily available. Eukaryotic expression systems for mammalian cells, yeast, and insect cells are well known in the art and are also commercially available.

Selection of an appropriate promoter to direct expression of a heterologous nucleic acid will depend on the particular application. Such a promoter may be positioned a distance from the heterologous transcription start site that is similar to the distance in its natural setting, although one of skill in the art will understand that some variation in this distance may be permitted without loss of promoter function.

In addition to a promoter, an expression vector typically contains a transcriptional or expression cassette that contains all elements required for expression of a nucleic acid in a host cell. Any conventional vectors known in the art that may be used for expression in eukaryotic or prokaryotic cells may be used to transport genetic information into a cell. A typical expression cassette thus contains a promoter operably linked to a nucleic acid sequence encoding the nucleic acid of choice and corresponding signals required for efficient processing, e.g., ribosome binding sites, polyadenylation, and translation termination. Additional elements may include enhancers and, for the case of genomic DNA as the structural gene, introns with functional splice donor and acceptor sites.

In addition to a promoter sequence, such as a promoter set forth herein, an expression cassette may also contain a transcription termination region downstream of the structural gene in order to provide for efficient termination of transcription. The termination region may be from the same gene as the promoter sequence, or it may be from a different gene. Markers such as fluorescent proteins, green or red fluorescent protein, β-gal, CAT, and the like can be included in the vectors as markers for vector transduction. Epitope tags or sequence tags may also be added to recombinant proteins to provide convenient methods of isolation.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, S V40 early promoter, SV40 late promoter, metallothionein promoter, murine mammary tumor virus promoter, Rous sarcoma virus promoter, polyhedrin promoter, or other promoters known in the art that may be effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. High levels of expression may be obtained from inducible promoters in the presence of an inducing agent. Some expression systems have markers such as thymidine kinase and dihydrofolate reductase, which provide gene amplification.

An expression vector may also include a replicon that functions in *E. coli*, an antibiotic resistance gene for selection of bacteria harboring recombinant plasmids, and unique restriction sites in nonessential regions of the plasmid to allow insertion of eukaryotic sequences. Any antibiotic resistance gene suitable for use with the present invention may be employed.

Standard transfection methods known in the art may be used to produce bacterial, mammalian, yeast, or insect cell lines that express large quantities of protein. Such cell lines may then be purified using standard techniques known in the art, and prokaryotic and/or eukaryotic cells may be transformed according to any method known in the art for introducing cloned genomic DNA, cDNA, synthetic DNA or other foreign genetic material into a host cell. Such methods may include, but are not limited to plasmid or viral vectors, calcium phosphate transfection, protoplast fusion, electroporation, biolistics, liposomes, microinjection, or any methods available in the art.

After an expression vector or transgene is introduced into a host cell, the cell may then be cultured under conditions optimum for expression of the desired protein, which may be recovered using standard techniques known in the art. Viral pathogens or viral proteins such as those described herein may then be purified for use in diagnostic assays, for making antibodies and immunogenic compositions, and for identification of antiviral compounds. Naturally occurring proteins may be purified from biological samples, such as a tissue sample from a bird infected with a virus as described herein, while recombinant proteins may be purified using any suitable methods or expression systems known in the art.

A number of procedures for purifying recombinant protein are available in the art. For example, proteins having established molecular adhesion properties can be reversibly fused to another protein. Additionally, a specific protein may be selectively adsorbed to a purification column and then freed from the column in a relatively pure form using appropriate ligands or substrates. The fused protein may then be removed by enzymatic activity. Protein may also be purified using affinity columns. Recombinant protein can be purified from any suitable source.

Purification of Protein from Recombinant Bacteria

Recombinant proteins may be expressed by bacteria in large amounts, for example using an inducible or constitutive promoter. Promoter induction using IPTG is an example of an inducible promoter system. Bacteria may be grown from fresh or frozen culture according to standard procedures known in the art.

Proteins expressed in bacteria may form insoluble aggregates called inclusion bodies. Suitable protocols for purification of protein inclusion bodies are known in the art. Lysing of bacterial for recovery of expressed proteins may be performed using any methods known in the art, which may include introduction of chemical buffers, sonication, mechanical disruption, and the like. Inclusion bodies may also be solubilized, and the lysed cell suspension may be centrifuged to remove unwanted cellular debris. Inclusion body proteins may be renatured by dilution or dialysis with an appropriate buffer.

Recombinant proteins may also be obtained from bacteria periplasm. After lysis of bacterial cells, the periplasmic fraction of the bacteria may be isolated by any methods known in the art. Recombinant proteins present in the supernatant may be separated from host proteins by standard separation techniques well known to those of skill in the art.

Proteins may be separated using any techniques known in the art, for example, solubility fractionation or size differential filtration, which isolates a protein on the basis of molecular weight using filtration through membranes of different pore size. Column chromatography may be used for isolation of a protein from other proteins on the basis of size, net surface charge, hydrophobicity, or affinity for ligands or substrates. In addition, antibodies raised against a protein of interest may be conjugated to a column and the proteins immunopurified. All of these methods are well known in the art. It will be apparent to one of skill that chromatographic techniques may be performed on any scale and using any appropriate commercial equipment.

Antibody Production

Methods of producing polyclonal and monoclonal antibodies that react specifically with viral proteins, virus particles, and/or nucleic acids are known in the art. Such techniques may include antibody preparation by selection of antibodies from recombinant antibody libraries in phage or other vectors, as well as preparation of polyclonal and monoclonal antibodies by immunizing rabbits or mice.

A number of antigens or antigenic regions comprising a viral protein or portions thereof, virus particles, and/or nucleic acids may be used to produce antibodies specifically reactive to a desired viral pathogen. For example, a recombinant viral protein or an antigenic fragment thereof, may be isolated using any methods described herein or known in the art. Recombinant proteins may be expressed in prokaryotic or eukaryotic cells and purified as described herein. Monoclonal and/or polyclonal antibodies may be produced using naturally occurring (in pure or impure form) or recombinant proteins using methods known in the art. Synthetic peptides derived from a viral sequence may also be used to generate antibodies and may be conjugated to a carrier protein and injected into an animal capable of producing antibodies (e.g., rabbit).

Methods of production of polyclonal antibodies are known to those of skill in the art. For example, an inbred strain of mice or rabbits may be immunized with a protein using a standard adjuvant, such as an adjuvant described herein, using a standard immunization protocol known in the art. When appropriately high titers of antibody to the protein are obtained, antisera may be prepared and enrichment performed to obtain antibodies reactive to the protein.

Monoclonal antibodies may also be obtained by various methods known in the art. For example, spleen cells from an animal immunized with a desired antigen may be immortalized, commonly by fusion with a myeloma cell or through transformation with Epstein Barr Virus (EBV), oncogenes, or retroviruses, or other methods well known in the art. The immortalized cells may then be screened for production of antibodies of the desired specificity and affinity for the antigen. Yield of the monoclonal antibodies produced by such cells may be enhanced by various techniques known in the art, for example by injection into the peritoneal cavity of a vertebrate host.

Monoclonal antibodies and polyclonal sera may be collected and titered against the desired antigen or protein in an immunoassay, for example, a solid phase immunoassay with the protein immobilized on a solid support. Antibodies specific only for a particular viral protein may also be made by subtracting out other cross-reacting proteins. In this manner, antibodies that bind only to the protein of choice may be obtained.

Once the specific antibodies against the desired viral antigen, such as protein, virus, and/or nucleic acid are available, the desired antigen may be detected using a variety of immunoassay methods. The antibody may also be used therapeutically.

Protein either associated with or distinct from a viral particle as described herein may be detected and/or quantified using any of a number of well recognized immunological binding assays. Viral particles may be detected based on an epitope defined by the viral proteins as presented in a viral particle and/or an epitope defined by a viral protein that is separate from a viral particle (e.g., such as may be present in an infected cell). Immunological assays may use an antibody that specifically binds to a protein or antigen of choice. The antibody may be produced by any of a number of methods well known to those of skill in the art. Immunoassays may also use a labeling agent to specifically bind to the complex formed by the antibody and antigen for detection purposes. The labeling agent may itself be one of the moieties comprising the antibody/antigen complex. Thus, the labeling agent may be a labeled viral protein nucleic acid or a labeled antiviral antibody. Alternatively, the labeling agent may be a third moiety, such as a secondary antibody, that specifically binds to the antibody/antigen complex. A secondary antibody may be specific to antibodies of the species from which the first antibody is derived. A labeling agent can be modified with a detectable moiety, such as biotin, to which another molecule can specifically bind, such as streptavidin. A variety of detectable moieties are well known to those skilled in the art.

Immunoassays for detecting viral protein, virus, and/or nucleic acid in samples are well known in the art. Such assays may be either competitive or noncompetitive, and may be either quantitative or non-quantitative. Noncompetitive immunoassays are assays in which antigen may be directly detected and, in some instances, the amount of antigen directly measured. In competitive assays, viral antigen present in a sample is detected indirectly by a detectable signal associated with a known, added (exogenous) viral antigen displaced from an antiviral antigen antibody by the viral antigen present in a sample. In this manner, such assays can also be adapted to provide for an indirect measurement of the amount of viral antigen present in the sample. Competitive binding immunoassays may also be used to determine cross-reactivity, in which any cross-reacting antibodies may be removed from pooled antisera. Additional assay types, including but not limited to western blot or liposome immunoassays may also be used in accordance with the present invention.

One of skill in the art will appreciate that it is often desirable to minimize nonspecific binding in immunoassays. Particularly, where the assay involves an antigen or antibody immobilized on a solid substrate it is desirable to minimize the amount of nonspecific binding to the substrate. Means of reducing such non-specific binding are well known to those of skill in the art.

An assay as described herein may include a label or detectable group that does not significantly interfere with the specific binding of the antibody used in the assay. A detectable group may be any material having a detectable physical or chemical property. Such detectable labels are known in the art and generally, any label useful in such methods may be applied to the present invention. Thus, a "label" as used herein may be any composition detectable by spectroscopic, photochemical, biochemical, immunochemical, electrical, optical or chemical means. Useful labels in the present invention may include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase, and/or any others known in the art and used in ELISA), and colorimetric labels such as colloidal gold or colored glass or plastic beads (e.g., polystyrene, polypropylene, latex, etc.).

A label in accordance with the invention may be coupled directly or indirectly to the desired component of the assay according to methods well known in the art. As described above, a wide variety of labels may be used, with the choice of label depending on sensitivity, ease of conjugation with the compound, stability requirements, or available instrumentation, among others.

Non-radioactive labels may be attached by indirect means. Generally, a ligand molecule (e.g., biotin) is covalently bound to the molecule. The ligand may then bind to another molecule (e.g., streptavidin), which may be either inherently detectable or covalently bound to a signal system, such as a detectable enzyme, a fluorescent compound, or a chemiluminescent compound. The ligands and their corresponding targets may be used in any suitable combination with antibodies that recognize a viral antigen, or secondary antibodies that recognize an antiviral antigen. The molecules may also be conjugated directly to signal generating compounds, e.g., by conjugation to an enzyme or fluorophore. Enzymes of interest to be used as labels may be hydrolases, for example phosphatases, esterases and glycosidases, or oxidotases, such as peroxidases. Fluorescent compounds may include fluorescein and its derivatives, rhodamine and its derivatives, dansyl, umbelliferone, and the like. Chemiluminescent compounds may include luciferin, 2,3-dihydrophthalazinediones, e.g., luminol, or others known in the art.

Means of detecting labels are well known to those of skill in the art and will depend on the type of label used. For example, autoradiography may be used to detect a radioactive label, or fluorochromes may be used to detect a fluorescent label. Fluorescence may be detected visually, for example by electronic detectors such as charge coupled devices (CCDs) or photomultipliers, and the like. Similarly, enzymatic labels may be detected by providing the appropriate substrates for the enzyme and detecting the resulting reaction product. Colorimetric or chemiluminescent labels may be detected by observing a color associated with a particular label. In some embodiments, an assay formats may not require the use of a labeled component but rather may be detected by simple visual inspection.

Pharmaceutical/Immunogenic Compositions and Administration Thereof

In some aspects, recombinant vectors comprising one or more transgenes expressing one or more viral proteins or peptides or fragments thereof as described herein may be used as pharmaceutical compositions or immunogenic compositions for administering to a subject such as a chicken or other poultry in order to provide protection from one or more viruses. For example, an immunogenic composition as described herein comprise a recombinant vector with one or more transgenes as described herein which are inserted into the viral genome, for example in an intergenic region flanked by HVT10 (UL3) and HVT11 (UL4) in the unique long region of the genome, and/or in an intergenic region flanked by HVT86 (US10) and HVT87 (Sorf3) in the unique short region of the genome. In other aspects, proteins or peptides and immunogenic fragments thereof, and/or polynucleotides, as well as antiviral antibodies and/or T cells, may be incorporated into pharmaceutical compositions or immunogenic compositions (e.g., vaccines). In another embodiment, an immunogenic composition according to the invention may comprise at least a third transgene, a fourth transgene, or the like, which may encode additional viral proteins. In such a way, it is possible to provide an immunogenic composition to a subject such as poultry that provides protection from any desired number of viruses. Whole virus vaccine (live and attenuated, or replication incompetent, or killed) or subunit vaccines, such as structural or non-structural viral proteins or immunogenic fragments thereof, can be used to treat or prevent viral infections by eliciting an immune response in a subject. Alternatively, a pharmaceutical composition may comprise an antigen-presenting cell transfected with a viral polynucleotide such that the antigen-presenting cell expresses a viral peptide.

Immunogenic compositions in accordance with the invention may be designed to generate antibody immunity and/or cellular immunity in a subject. Such compositions may comprise one or more such compounds along with a non-naturally occurring pharmaceutically acceptable carrier. In other embodiments, an immunogenic composition in accordance with the invention may include more than one adjuvants or pharmaceutically acceptable carriers such that at least one is non-naturally occurring. A pharmaceutically acceptable carrier or adjuvant may be any substance that enhances an immune response in a subject to an exogenous antigen, including but not limited to, adjuvants, liposomes, biodegradable microspheres. A pharmaceutically acceptable carrier or adjuvant may contain a substance designed to protect the antigen from rapid catabolism, such as aluminum hydroxide or mineral oil, or a stimulator of immune responses, such as proteins derived from *Bortadella pertussis* or *Mycobacterium tuberculosis*. Commercially available adjuvants may include for example, Freund's Incomplete Adjuvant and Complete Adjuvant, Merck Adjuvant 65, aluminum salts such as aluminum hydroxide gel (alum) or aluminum phosphate; CpG oligonucleotides, salts of calcium, iron or zinc; an insoluble suspension of acylated tyrosine; acylated sugars; cationically or anionically derivatized polysaccharides; polyphosphazenes; biodegradable microspheres; and monophosphoryl lipid A. One of skill in the art will be able to identify appropriate pharmaceutically acceptable carriers for use with the present invention.

Pharmaceutical or immunogenic compositions and/or vaccines within the scope of the present invention may also contain other compounds, which may be biologically active or inactive. For example, one or more immunogenic portions of other antigens may be present, either incorporated into a fusion polypeptide or as a separate compound, within a composition or vaccine according to the invention. In some embodiments, polypeptides useful with the present invention may be conjugated to other macromolecules. Pharmaceutical or immunogenic compositions and vaccines may generally be used for prophylactic and/or therapeutic purposes. For example, in accordance with the invention, a composition as described herein may be provided to a subject, such as a bird, prior to infection with or exposure to a virus in order to provide protection against infection with one or more viruses or development of symptoms of infection. In other embodiments, such a composition may be provided to a subject, such as a bird, after infection with or exposure to one or more viruses in order to provide treatment of the viruses in the subject, such as by reducing or eliminating infection in the subject.

Nucleic acid vaccines encoding a genome, structural or non-structural protein, or a fragment thereof of a virus described herein may also be used to elicit an immune response to treat or prevent viral infection. Numerous gene delivery techniques are well known in the art. Appropriate nucleic acid expression systems may contain the necessary DNA sequences for expression in a subject (such as a suitable promoter and termination signal). In some embodiments, a DNA as described herein may be introduced using a viral expression system (e.g., Marek's disease virus or HVT), which may involve the use of a non-pathogenic, replication competent virus.

Pharmaceutical or immunogenic compositions may be provided in single-dose or multi-dose containers, such as sealed ampoules or vials. Such containers may be sealed to preserve sterility of the composition until use. In general, compositions as described herein may be stored as suspensions, solutions, or emulsions in oily or aqueous vehicles. Alternatively, such a composition may be stored in a freeze-dried condition requiring only the addition of a sterile liquid carrier immediately prior to use.

As described herein, an immunogenic composition may be combined with a pharmaceutically acceptable carrier. The selection of a suitable carrier may be determined in part by the particular composition being administered (e.g., nucleic acid, protein, modulatory compounds, or transduced cell), as well as by the particular method used to administer the composition. Accordingly, a wide variety of suitable formulations of pharmaceutical or immunogenic compositions are available that may of use in the present invention. Administration may be in any convenient manner, e.g., by injection, oral administration, inhalation, transdermal application, or rectal administration. Injection of a recombinant vector or an immunogenic composition as described herein may be provided to a subject such as poultry in a single administration or dose, or may be administered more than once, such as repeated doses.

Formulations suitable for parenteral administration, such as, for example, by intraarticular (in the joints), intravenous, intramuscular, intradermal, intraperitoneal, in ovo, and subcutaneous routes, include aqueous and non-aqueous, isotonic sterile injection solutions, which can contain antioxidants, buffers, bacteriostats, and solutes that render the formulation isotonic with the blood of the intended subject, and aqueous and nonaqueous sterile suspensions that can include suspending agents, solubilizers, thickening agents, stabilizers, and preservatives. In the practice of this invention, compositions may be administered, for example, by intravenous infusion, orally, topically, intraperitoneally, intravesically or intrathecally.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic, or weakly hypertonic with the blood of a subject, suspending agents, thickening agents, and/or preservatives. Alternatively, compositions of the present invention may be formulated as a lyophilizate. Compounds may also be encapsulated within liposomes using methods known in the art.

Injection solutions and suspensions may be prepared from sterile powders, granules, and tablets as described herein.

Cells transduced by nucleic acids for ex vivo therapy may also be administered intravenously or parenterally as described above. An injection as described herein may involve a suspension of one or more of a killed, inactivated, attenuated, or otherwise non-virulent virus culture, purified or non-purified solution of a viral protein, or a nucleic acid as described herein. An injection solution may also contain a pharmaceutically acceptable carrier as described herein.

Formulations suitable for oral administration may consist of (a) liquid solutions, such as an effective amount of the packaged viral protein or nucleic acid suspended in diluents, such as water, saline or PEG 400; (b) capsules or tablets, each containing a predetermined amount of the active ingredient, as liquids, solids, granules or gelatin; (c) suspensions in an appropriate liquid; or (d) suitable emulsions. Tablet forms may include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms may comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, may be made into aerosol formulations to be administered via inhalation. Aerosol formulations may be placed into pressurized acceptable propellants, such as dichlorodifluoromethane, propane, nitrogen, and the like.

The dose administered to a subject in the context of the present invention should be sufficient to effect a beneficial therapeutic response in the subject over time. The dose will be determined by the efficacy of the particular vector employed and the condition of the subject, as well as the body weight and/or surface area of the patient to be treated. The size of the dose also may be determined by the existence, nature, and extent of any adverse side-effects that accompany the administration of a particular vector, or transduced cell type in a particular patient. For compositions comprising a vector as described herein, the effective amount of the vector to be administered may be determined in part based on circulating plasma levels of the vector, vector toxicities, health of the subject, and production of anti-vector antibodies.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the subject. Administration may be accomplished via single, multiple, or divided doses.

Immunological Detection of Polypeptides and Nucleic Acids

Immunoassays may be used to detect viral proteins, virus particles, and/or nucleic acids. Such assays may be useful for therapeutic and/or diagnostic applications, such as those described herein. Immunoassays are well known in the art and may be used to qualitatively or quantitatively analyze proteins, virus particles, and/or nucleic acids.

Assays for Viral Proteins and Antibodies to Viral Antigens

In one embodiment of the present invention, the presence of a virus as described herein, a viral nucleic acid, or a viral protein in a sample may be determined by an immunoassay. Enzyme-mediated immunoassays such as immunofluorescence assays (IFA), enzyme linked immunosorbent assays (ELISA), capture assays, micro-agglutination tests, and immunoblotting assays (e.g., western blot) can be readily adapted to accomplish detection of a virus or viral proteins. An ELISA method may be effective for detection of a virus or viral protein as described herein. Such an ELISA may, for example, have steps such as: (1) bind an antiviral antibody or antigen to a substrate; (2) contact the bound receptor with a biological sample containing a virus, a viral antigen, a viral protein, or antibodies to the virus; (3) contact the biological sample with an antibody bound to a detectable moiety (e.g., horseradish peroxidase enzyme or alkaline phosphatase enzyme); (4) contact the biological sample with the substrate for the enzyme; (5) contact the biological sample with a detecting reagent, such as a color reagent; (6) observe a detectable result. In some embodiments, a biological sample suitable for use in such an ELISA may be blood or other fluids. In another embodiment, an ELISA as described herein may detect a virus or viral protein in a tissue sample. Such methods may be readily modified by those of skill to detect the presence of an antiviral antibody in a sample, or a specific viral protein, as well as the virus. In certain embodiments, an ELISA according to the invention may detect the presence of an antiviral antibody.

ELISA assays as described herein may include a nitrocellulose strip impregnated with a viral protein as described herein. The nitrocellulose strip may produce a visual result when contacted with a test sample containing antiviral nucleoprotein antibodies. Such a test may identify a subject already having antibodies against a viral protein and thus the subject may have immunity to the virus. Administration of an immunogenic composition to prevent viral infection such as described herein may be unnecessary in such a subject and therefore, identification of subjects already having immunogenic antibodies may prevent unnecessary administration of an immunogenic compound to such a subject. In this regard, an embodiment of the present invention may involve identifying a subject lacking antiviral antibodies using an assay as described herein, such as an ELISA assay, and then providing an immunogenic composition as described herein to that subject in order to prevent viral infection. In another embodiment, a nitrocellulose strip for use in an ELISA according to the invention may be impregnated with an antibody, such as antiviral antibody, and may produce a visual result when contacted with a test sample containing a viral protein. Such a test may identify a subject infected with a virus as described herein.

Another immunologic technique that can be useful in the detection of a virus is a competitive inhibition assay. Such an assay utilizes monoclonal antibodies (MABs) reactive with a specific virus. A biological fluid (e.g., blood) from a subject may be contacted with a first antibody bound to a substrate, and a labeled monoclonal antibody contacted with the first antibody-virus complex. The amount of inhibition of monoclonal antibody binding is measured relative to a control.

As will be readily understood by one of skill in the art, a biological sample for use in the above assays may be taken directly from a subject or may be in a partially purified form. An antibody specific for a particular virus will react by binding to the virus as a primary reaction. Thereafter, a secondary reaction with an antibody bound to or labeled with a detectable moiety may also be added in order to enhance the detection of the primary reaction. Generally, in the secondary reaction, an antibody or other ligand which is reactive, either specifically or nonspecifically with a different binding site (epitope) of the virus will be selected for its ability to react with multiple sites on the complex of antibody and virus. Thus, for example, several molecules of the antibody in the secondary reaction can react with each complex formed by the primary reaction, making the primary reaction more detectable.

The detectable moiety can allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from any disclosed herein or available in the art.

Detecting the Presence of a Viral Nucleic Acid

In some embodiments, a viral infection as described herein may be detected based on the level of a particular RNA or DNA in a biological sample. Primers from a particular virus or viral pathogen may be used for detection, diagnosis, and determination of the presence of a virus. Any suitable primer may be used to detect genomic DNA or any sequence therein, an open reading frame or gene, or a protein of choice, using any appropriate methods known in the art. A suitable nucleic acid sequence may be used as single- or double-stranded probes or primers for detection of viral mRNA or cDNA generated therefrom, as may be present in a biological sample. Viral polynucleotides as described herein may also be used to generate additional copies of the polynucleotides, in order to generate antisense oligonucleotides, or as triple-strand forming oligonucleotides. For example, two oligonucleotide primers may be used in a PCR-based assay to amplify a portion of a viral cDNA derived from a biological sample, wherein at least one of the oligonucleotide primers is specific for (i.e., hybridizes to) the viral polynucleotide. Such primers may be any length sufficient to hybridize to and enable amplification of a viral nucleic acid as described herein, including at least or about 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 35 nucleotides, 40 nucleotides, 45 nucleotides, or 50 nucleotides; or from about 12 to about 50 nucleotides in length, 15 to 30 nucleotides in length, 15 to 25 nucleotides in length, or 20 to 30 nucleotides in length. DNA primers suitable for use with the present invention may be any primers described herein, such as those set forth as SEQ ID NOs:1-13. An amplified nucleotide, for example a cDNA, may then be separated and detected using techniques well known in the art, such as gel electrophoresis. Similarly, oligonucleotide probes that specifically hybridize to a viral polynucleotide may be used in a hybridization assay to detect the presence of a viral polynucleotide in a biological sample.

Nucleic acid probes or primers specific to a virus as described herein may be generated using the polynucleotide sequences disclosed herein. The probes are preferably at least about 12, 15, 16, 18, 20, 22, 24, or 25 nucleotide fragments or other polynucleotide sequence encoding a viral nucleic acid or polypeptide. Nucleic acid probes can be less than about 200 bp, 150 bp, 100 bp, 75 bp, 50 bp, 60 bp, 40 bp, 30 bp, 25 bp 2 kb, 1.5 kb, 1 kb, 0.5 kb, 0.25 kb, 0.1 kb, or 0.05 kb in length. The probes can be produced by, for example, chemical synthesis, PCR amplification, generation from longer polynucleotides using restriction enzymes, or other methods well known in the art. The polynucleotides described herein may also be used in methods or assays that involve the use of solid substrates, such as arrays. Such an array may have one or more different polynucleotides, which may be immobilized on the arrays using methods known in the art.

In some embodiments, a polynucleotide of the invention may be detectably labeled. Detectable labels may include, but are not limited to, radiolabels, fluorochromes, including fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4',7',4,7-hexachlorofluorescein (HEX), 5-carboxy fluorescein (5-FAM) or N,N,N',N'-tetramethyl-6-carboxyrho-damine (TAMRA); radioactive labels such as $^{32}P$, $^{35}S$, and $^{3}H$), and the like. In some embodiments, a detectable label may involve multiple steps (e.g., biotin-avidin, hapten-anti-hapten antibody, and the like).

In accordance with the invention, any suitable qualitative or quantitative methods known in the art for detecting specific viral nucleic acids (e.g., RNA or DNA) may be used. A viral nucleic acid as described herein may be detected by, for example, in situ hybridization in tissue sections, using methods that detect single base pair differences between hybridizing nucleic acid, by reverse transcriptase-PCR, or in northern blots containing poly A mRNA, or other methods well known in the art. For detection of viral polynucleotides in blood or blood-derived samples, methods that allow for detection of single base pair mismatches may be employed.

A viral nucleic acid sequence may be present in a biological sample obtained from an infected individual at relatively low levels, and thus amplification techniques known in the art (e.g., PCR) may be used to amplify the sequence prior to performing a hybridization assays.

Nucleic acid probes may be prepared using a viral genome as described herein. Such a probe may include at least about 8 nucleotides or more and may be prepared synthetically or by excision from recombinant polynucleotides. A probe as described herein may hybridize with a viral nucleic acid, and thus such a probe may be useful for detection of a particular virus in a biological sample. Probes as described herein may also be useful for identification of infected subjects, as well as for further characterization of viral genomes. A probe for detecting viral polynucleotides (natural or derived) may be of a specific length or have a sequence which allows the detection of unique viral sequences by hybridization. While about 6-8 nucleotides may be useful, longer sequences may be preferred, e.g., sequences of about 10-12 nucleotides, or about 20 nucleotides or more. One of skill in the art will be well aware how to make and use a probe as described herein.

Nucleic acid probes may be prepared using routine methods, including, but not limited to, automated oligonucleotide synthetic methods. A sequence useful for preparing such a probe may include a complement to any unique portion of a viral genome, for example a portion of the viral genome that allows for distinguishing a particular virus from other viruses that may be present in the sample. A probe as described herein may have complete complementarity to the target sequence of interest, or may have one or more mismatches. A probe useful in accordance with the invention having one of more mismatches will still hybridize to the target sequence of interest. For use of such probes as diagnostics, the biological sample to be analyzed may be treated prior to analysis, if desired, to extract the nucleic acids contained therein. The resulting nucleic acids from the sample may be subjected to gel electrophoresis or other size separation techniques. A probe may be labeled with a detectable label as described herein. Suitable labels, and methods for labeling probes are known in the art, and may include any labels described herein or others useful with the present invention.

A probe may be completely complementary to a viral genome or portion thereof (e.g., to all or a portion of a sequence encoding a viral protein as described herein). High stringency conditions may be desirable in order to prevent or at least minimize false positive results. The stringency of hybridization may be determined by a number of factors during hybridization and washing, including temperature, ionic strength, length of time, and concentration of reagents. A probe or nucleic acid from a sample may be provided in solution for such assays, or may be affixed to a support (e.g., solid or semi-solid support). Examples of supports that may be used include but are not limited to nitrocellulose (e.g., membrane or microtiter well form), polyvinyl chloride (e.g., sheets or microtiter wells), polystyrene latex (e.g., beads or microtiter plates, polyvinylidine fluoride, diazotized paper, nylon membranes, activated beads, and Protein A beads).

In one embodiment, a probe or sample nucleic acid may be provided on an array for detection. Arrays may be created by, for example, spotting polynucleotide probes onto a substrate (e.g., glass, nitrocellulose, and the like) in a two-dimensional matrix or array. The probes may be bound to the substrate by either covalent bonds or by non-specific interactions, such as hydrophobic interactions. Samples of polynucleotides can be detectably labeled (e.g., using radioactive or fluorescent labels) and then hybridized to the probes. Double stranded polynucleotides, comprising the labeled sample polynucleotides bound to probe polynucleotides, may be detected once the unbound portion of a sample is removed. Techniques for constructing arrays and methods of using these arrays are known in the art. Arrays may be used for a single sample to be analyzed for the presence of two or more nucleic acid target regions. In such a case, the probes for each of the target regions, as well as controls (both positive and negative) may be provided on a single array. Arrays thus facilitate rapid and convenience analysis.

Diagnostic Tests and Kits

The invention further provides diagnostic reagents and kits comprising one or more such reagents for use in a variety of diagnostic assays, including for example, immunoassays such as ELISA and "sandwich"-type immunoassays, as well as nucleic acid assays, e.g., PCR assays. In a related embodiment, an assay may be performed in a flow-through or strip test format, wherein the binding agent is immobilized on a membrane, such as nitrocellulose. Such kits may preferably include at least a first peptide, or a first antibody or antigen binding fragment of the invention, a functional fragment thereof, or a cocktail thereof, or a first oligonucleotide pair, and means for signal generation. In some embodiments, a kit may comprise an immunogenic composition, such as a recombinant virus as described herein. Reagents and other compounds, such as a pharmaceutically acceptable carrier may be included in the kit. An immunogenic composition when provided in such a kit may be in a solution such as in a pre-measured dose or amount, or may be a dry composition, such as in desiccated or lyophilized form suitable for rehydration or resuspension. The kit components may be pre-attached to a solid support, or may be applied to the surface of a solid support when the kit is used. The signal generating means may come pre-associated with an antibody or nucleic acid of the invention or may require combination with one or more components, e.g., buffers, nucleic acids, antibody-enzyme conjugates, enzyme substrates, or the like, prior to use.

Kits may also include additional reagents, e.g., blocking reagents for reducing nonspecific binding to the solid phase surface, washing reagents, enzyme substrates, enzymes, and the like. The solid phase surface may be in the form of microtiter plates, microspheres, or other materials suitable for immobilizing nucleic acids, proteins, peptides, or polypeptides. An enzyme that catalyzes the formation of a chemiluminescent or chromogenic product or the reduction of a chemiluminescent or chromogenic substrate is one such component of the signal generating means. Such enzymes are well known in the art. Where a radiolabel, chromogenic, fluorigenic, or other type of detectable label or detecting means is included within the kit, the labeling agent may be provided either in the same container as the diagnostic or therapeutic composition itself, or may alternatively be placed in a second distinct container into which this second composition may be placed and suitably aliquoted. Alternatively, the detection reagent and the label may be prepared in a single container means.

Definitions

As used herein "Marek's disease virus" or "MDV" refers to any alphaherpesvirus of the genus Mardivirus, including the Herpesvirus of Turkeys (HVT). In a specific embodiment, the invention relates to the Marek's disease virus, its genetic components, genes, and proteins produced thereby. As used herein, such a virus may include the genetic components of the virus, i.e., the genome and transcripts thereof, proteins encoded by the genome (including structural and nonstructural proteins), and functional or nonfunctional viral particles. The polynucleotide and polypeptide sequences encoding such viruses are well known in the art and would be easily found by one of skill in the art. A polynucleotide or polypeptide sequence as described herein may be from a bird including, but not limited to, poultry such as chickens, quails and turkeys. The nucleic acids and proteins of the invention include both naturally occurring or recombinant molecules.

As used herein, "poultry" refers to a domestic or commercial bird kept for the eggs they produce, as well as their meat and feathers. In some embodiments, poultry may include a bird from the order Galliformes, which includes chickens, quails, and turkeys, and may also include geese, ducks, swan, guinea, pigeons, and the like.

As used herein, "viral proteins" or "viral polypeptides" refers to a protein encoded by a virus described herein, including structural and non-structural proteins. Such proteins may include naturally occurring or non-naturally occurring viral proteins from MDV, NDV, and/or IBDV, including VP2, F, and/or HN proteins. As used herein, an "antigen" refers to a viral protein or polypeptide, such as a viral polypeptide, as well as viral particles. In some embodiments, an antigen in accordance with the invention may also be a viral nucleic acid.

As used herein, the terms "treatment," "treating," and "treat" are defined as acting upon a disease, disorder, or condition with an agent to reduce or ameliorate the pharmacologic and/or physiologic effects of the disease, disorder, or condition and/or its symptoms. "Treatment," as used herein, covers any treatment of a disease in a subject or host (e.g., an animal of veterinary interest), and includes: (a) reducing the risk of occurrence of the disease in a subject determined to be predisposed to the disease but not yet diagnosed as infected with the disease, (b) impeding the development of the disease, and (c) relieving the disease, i.e., causing regression of the disease and/or relieving one or more disease symptoms. "Treatment" is also meant to encompass delivery of an inhibiting agent to provide a pharmacologic effect, even in the absence of a disease or condition. For example, "treatment" encompasses delivery of a disease or pathogen inhibiting agent that provides for enhanced or desirable effects in the subject (e.g., reduction of pathogen load, reduction of disease symptoms, etc.).

As used herein, the terms "prophylactically treat" or "prophylactically treating" refers to completely or partially preventing a disease or symptom thereof and/or may be therapeutic in terms of a partial or complete cure for a disease and/or adverse effect attributable to the disease.

As used herein, a "transgene" refers to a segment of DNA containing a heterologous coding sequence or other genetic material for introduction from one organism into another. For instance, in certain embodiments, a transgene according to the present invention may comprise an antigenic coding sequence, such as a viral gene, or a sequence encoding a viral protein.

As used herein, the term "host," "subject," "patient," or "organism" may include animals, particularly birds, especially poultry. For veterinary applications, a birds may be from the order Galliformes, which includes chickens, quails and turkeys, and the like. The term "living host" refers to a host as noted above or another organism that is alive. The term may also refer to the entire host or organism and not just a part excised (e.g., a brain or other organ) from the living host. These terms also include an individual in all stages of development, including embryonic and fetal stages.

As used herein, a "biological sample" or "sample" may include blood and blood parts including, but not limited to serum, plasma, platelets, or red blood cells; sputum, cloacal swabs, mucosa, tissue, cultured cells, including primary cultures, explants, and transformed cells; biological fluids, stool, and urine. A biological sample may also include sections of tissues such as biopsy and autopsy samples, and frozen sections taken for histologic purposes. A biological sample may be obtained from a eukaryotic organism, such as a bird, including, but not limited to, a bird from the order Galliformes, such as chickens, quails and turkeys. Any tissue appropriate for use in accordance with the invention may be used, for instance, skin, brain, spinal cord, adrenals, pectoral muscle, lung, heart, liver, crop, proventriculus, ventriculus, duodenum, small intestine, large intestine, cloaca, kidney, bursa of fabricus, spleen, pancreas, adrenal gland, bone marrow, lumbosacral spinal cord, or blood.

The term "isolated" means a substance that has been substantially separated from, or enriched relative to, other substances with which it occurs in nature. Isolated substances are usually at least about 80%, at least 90% pure, at least 98% pure, or at least about 99% pure, by weight.

The term "unit dosage form," as used herein, refers to physically discrete units suitable as unitary dosages for animal subjects, each unit containing a predetermined quantity of a compound (e.g., an antiviral compound, as described herein) calculated in an amount sufficient to produce the desired effect in association with a pharmaceutically acceptable diluent, carrier, or vehicle. The specifications for unit dosage forms depend on the particular compound employed, the route and frequency of administration, the effect to be achieved, and the pharmacodynamics associated with each compound in the host.

As used herein, a "pharmaceutically acceptable carrier," "pharmaceutically acceptable adjuvant," or "adjuvant" refers to an agent that modifies the effect of other agents and is useful in preparing an immunogenic composition that is generally safe, non-toxic, and neither biologically nor otherwise undesirable. Such an agent may be added to an immunogenic composition to modify the immune response of a subject by boosting the response such as to give a higher amount of antibodies and longer-lasting protection. Such an agent may include an excipient, diluent, carrier, or adjuvant that is acceptable for veterinary or pharmaceutical use. Such an agent may be non-naturally occurring, or may be naturally occurring, but not naturally found in combination with other agents in the immunogenic composition.

As used herein, an "immunogenic composition" or "pharmaceutical composition" or "vaccine" is meant to encompass a composition suitable for administration to a subject, such as an avian subject. In general an "immunogenic composition" is sterile, and preferably free of contaminants that are capable of eliciting an undesirable response within the subject (e.g., the compound(s) in the immunogenic composition is pharmaceutical grade). Immunogenic compositions may be designed for administration to subjects in need thereof via a number of different routes of administration including in ovo, oral, intravenous, buccal, rectal, parenteral, intraperitoneal, intradermal, intracheal, intramuscular, subcutaneous, inhalational, and the like.

The term "therapeutically effective amount," "effective amount," or "therapeutically effective dose" as used herein refers to a dose that produces an effect for which it is administered. Such a dose or amount may also refer to the amount of an embodiment of the agent (which may be referred to as a compound, an inhibitory agent, and/or a drug) being administered that will relieve to some extent one or more of the symptoms of the disease, i.e., infection, being treated, and/or that amount that will prevent, to some extent, one or more of the symptoms of the disease, i.e., infection, that the host being treated has or is at risk of developing. The exact dose will depend on the purpose of the treatment, and one of skill in the art will be able to determine such a dose using techniques known in the art.

As used herein, an "antibody" refers to a polypeptide comprising a framework region from an immunoglobulin gene or fragments thereof that specifically binds and recognizes an antigen. The recognized immunoglobulin genes may include the kappa, lambda, alpha, gamma, delta, epsilon, and mu constant region genes, as well as the myriad immunoglobulin variable region genes. Light chains may be classified as either kappa or lambda. Heavy chains may be classified as gamma, mu, alpha, delta, or epsilon, which in turn define the immunoglobulin classes, IgY, IgG, IgM, IgA, IgD, and IgE, respectively.

An exemplary immunoglobulin (antibody) structural unit may comprise a tetramer, with each tetramer composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain and variable heavy chain refer to these light and heavy chains.

Antibodies exist, e.g., as intact immunoglobulins or as a number of well-characterized fragments produced by digestion with various peptidases. While various antibody fragments are defined in terms of the digestion of an intact antibody, one of skill will appreciate that such fragments may be synthesized de novo either chemically or by using recombinant DNA methodology. Thus, the term "antibody," as used herein, also includes antibody fragments either produced by the modification of whole antibodies, or those synthesized de novo using recombinant DNA methodologies or those identified using other methods known in the art.

For preparation of antibodies, e.g., recombinant, monoclonal, or polyclonal antibodies, many technique known in the art may be used. The genes encoding the heavy and light chains of an antibody of interest can be cloned from a cell and used to produce a recombinant monoclonal antibody. Gene libraries encoding heavy and light chains of monoclonal antibodies may also be used. Random combinations of the heavy and light chain gene products generate a large pool of antibodies with different antigenic specificity. Techniques for the production of single chain antibodies or recombinant antibodies are found in the art and may be adapted to produce antibodies to polypeptides according to the invention. Phage display technology may also be used to identify antibodies and heteromeric fragments that specifically bind to selected antigens. Antibodies may also be made bispecific, i.e., able to recognize two different antigens, or heteroconjugates, e.g., two covalently joined antibodies, or immunotoxins.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins. Thus, under particular immunoassay conditions, a specified antibody may bind to a particular protein at least two times the background and more typically more than 10 to 100 times background. Specific binding to an antibody under such conditions requires an antibody that is selected by virtue of its specificity for a particular protein. For example, polyclonal antibodies raised to a virus as described herein, polymorphic variants, alleles, orthologs, and variants thereof, or splice variants, or portions thereof, may be selected to obtain only those polyclonal antibodies that are specifically immunoreactive with such viruses and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein. Preferred antibodies are those which can distinguish a viral protein as described herein, with respect to proteins encoded by the VP2, F, and/or HN genes.

The phrase "functional effects" in the context of assays for testing compounds that modulate activity of a virus as described herein includes the determination of a parameter that is indirectly or directly under the influence of such a virus, e.g., a phenotypic or chemical effect. "Functional effects" may include in vitro, in vivo, and ex vivo activities and may be measured by any means known to those skilled in the art, such as changes in spectroscopic characteristics, shape, chromatographic, or solubility properties for a protein, measuring inducible markers or transcriptional activation of a protein; measuring binding activity or binding assays, e.g. binding to antibodies; measuring changes in ligand or substrate binding activity, measuring viral replication, measuring cell surface marker expression, measurement of changes in protein levels, measurement of RNA stability, identification of downstream or reporter gene expression via, for example, chemiluminescence, fluorescence, colorimetric reactions, antibody binding, and/or inducible markers.

The terms "inhibitors," activators," and "modulators" of viral nucleic acid and polypeptide sequences are used to refer to activating, inhibitory, or modulating molecules identified using in vitro and in vivo assays of the viral nucleic acid and polypeptide sequences. Inhibitors are compounds that may bind to, partially or totally block activity, decrease, prevent, delay activation, inactivate, desensitize, or down regulate the activity or expression of a virus. Activators refer to compounds that increase, open, activate, facilitate, enhance activation, sensitize, agonize, or up regulate viral activity. Inhibitors, activators, or modulators also include genetically modified versions of a virus as described herein, e.g., versions with altered activity, as well as naturally occurring and synthetic ligands, substrates, antagonists, agonists, antibodies, peptides, cyclic peptides, nucleic acids, antisense molecules, ribozymes, small chemical molecules and the like. Assays for inhibitors and activators include, e.g., expressing a virus os the invention in vitro, in cells, or cell membranes, applying putative modulator compounds, and then determining the functional effects on activity, as described herein.

Test samples or assays comprising a virus of the invention that are treated with a potential activator, inhibitor, or modulator may be compared to a control sample lacking the inhibitor, activator, or modulator in order to determine the extent of inhibition. Control samples to which a test sample or assay is compared may be assigned a relative protein activity value of 100%. Inhibition of virus is achieved when the activity value of the test sample relative to the control sample is less than about 80%, including about 75%, about 70%, about 65%, about 60%, about 55%, about 50%, about 45%, about 40%, about 35%, about 30%, about 25%, about 20%, about 15%, about 10%, about 5%, and about 0%.

The terms "identical" or "percent identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., the NCBI web site found at ncbi.nlm.nih.gov/BLAST/ or the like). Such sequences are then referred to as "substantially identical." This definition also refers to, or applies to, the compliment of a particular sequence. The definition may also include sequences that have deletions, additions, and/or substitutions.

For sequence comparison, one sequence typically serves as a reference sequence, to which other sequences are compared. When using a sequence comparison algorithm, reference and comparison sequences may be entered into a computer, and sequence algorithm program parameters are selected as desired. Percent sequence identities are then generated for the comparison sequences relative to the reference sequence, based on the parameters selected. An example of an algorithm that may be suitable for determining percent sequence identity and sequence similarity are the BLAST and BLAST 2.0 algorithms, which are described in Altschul et al., (*Nuc Acids Res* 25:3389-3402, 1977) and Altschul et al., (*J Mol Biol* 215:403-410, 1990), respectively.

BLAST and BLAST 2.0 are well known in the art and may be used to determine percent sequence identity for any nucleic acids or proteins, such as those described herein.

As used herein, the term "nucleic acid" refers to a single or double-stranded polymer of deoxyribonucleotide bases or ribonucleotide bases read from the 5' to the 3' end. A "nucleic acid" may also optionally contain non-naturally occurring or altered nucleotide bases that permit correct read through by a polymerase and do not reduce expression of a polypeptide encoded by that nucleic acid. The term "nucleotide sequence" or "nucleic acid sequence" refers to both the sense and antisense strands of a nucleic acid as either individual single strands or in the duplex. The term "ribonucleic acid" (RNA) is inclusive of RNAi (inhibitory RNA), dsRNA (double stranded RNA), siRNA (small interfering RNA), mRNA (messenger RNA), miRNA (micro-RNA), tRNA (transfer RNA, whether charged or discharged with a corresponding acylated amino acid), and cRNA (complementary RNA). The terms "nucleic acid segment," "nucleotide sequence segment," or more generally, "segment," will be understood by those in the art as a functional term that includes genomic sequences, ribosomal RNA sequences, transfer RNA sequences, messenger RNA sequences, operon sequences, and smaller engineered nucleotide sequences that express or may be adapted to express, proteins, polypeptides or peptides. The nomenclature used herein is that required by Title 37 of the United States Code of Federal Regulations § 1.822 and set forth in the tables in WIPO Standard ST.25 (1998), Appendix 2, Tables 1 and 3.

The term "gene" refers to components that comprise viral DNA or RNA, cDNA, viral intron and exon DNA, artificial viral DNA polynucleotide, or other DNA that encodes a viral peptide, viral polypeptide, viral protein, or viral RNA transcript molecule, and the genetic elements that may flank the coding sequence that are involved in the regulation of expression, such as, promoter regions, 5' leader regions, 3' untranslated region that may exist as native genes or transgenes in a viral genome. The gene or a fragment thereof can be subjected to polynucleotide sequencing methods that determines the order of the nucleotides that comprise the gene.

Polynucleotides as described herein may be complementary to all or a portion of a viral gene sequence, including a promoter, intron, coding sequence, exon, 5' untranslated region, and 3' untranslated region.

A particular nucleic acid sequence may also encompass "splice variants." Similarly, a particular protein encoded by a nucleic acid implicitly encompasses any protein encoded by a splice variant of that nucleic acid. "Splice variants" are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Macromolecular structures such as polypeptide structures may be described in terms of various levels of organization. "Primary structure" refers to the amino acid sequence of a particular peptide. "Secondary structure" refers to locally ordered, three dimensional structures within a polypeptide. These structures are commonly known as domains, for example enzymatic domains, extracellular domains, transmembrane domains, pore domains, or cytoplasmic tail domains. Domains are portions of a polypeptide that form a compact unit of the polypeptide. Exemplary domains include domains with enzymatic activity. A domains may be made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. In some embodiments, recombinant sequences may also include nucleic acids, proteins, or recombinant genomes, such as viral genomes. Recombinant viral vectors as described herein may contain transgenes that are operatively linked to a heterologous promoter in order to effect transcription of the transgene.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein). Heterologous may also refer to a viral sequence, such as a gene or transgene, or a portion thereof, being inserted into a viral genome in which it is not typically found, or a gene introduced into an organism in which it is not typically found.

The phrase "stringent hybridization conditions" refers to conditions under which a probe will hybridize to its target subsequence, typically in a complex mixture of nucleic acids, but to no other sequences. Stringent conditions may be sequence-dependent and will be different in different circumstances. Longer sequences hybridize specifically at higher temperatures. Stringent conditions may be achieved with the addition of destabilizing agents such as formamide.

Appropriate stringency conditions that promote DNA hybridization are well known to one of skill in the art and may include, for example, 6× sodium chloride/sodium citrate (SSC) at about 45° C., followed by a wash of 2×SSC at 50° C. The salt concentration in the wash step may be selected from a low stringency of approximately 2×SSC at 50° C. to a high stringency of about 0.2×SSC at 50° C. The temperature in the wash step may be increased from low stringency conditions at room temperature, about 22° C., to high stringency conditions at about 65° C. The temperature and/or salt conditions may be varied as appropriate for optimum results. In accordance with the invention, a nucleic acid may exhibit at least from about 80% to about 100% sequence identity with one or more nucleic acid molecules as described herein, for example at least from about 80%, about 85%, about 90%, about 95%, about 98%, about 99%, or about 100% sequence identity.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" may include hybridization in a buffer of 40% formamide, 1 M NaCl, 1% SDS at 37° C., and a wash in 1×SSC at 45° C. A positive hybridization may be at least twice the background. Those of ordinary skill in the art will recognize that alternative hybridization and wash conditions may be utilized to provide conditions of similar stringency or will be able to determine optimum conditions as appropriate.

For PCR, a temperature of about 36° C. is typical for low stringency amplification, although annealing temperatures may vary depending on primer length. For high stringency PCR amplification, a temperature of about 62° C. is typical, although high stringency annealing temperatures can vary depending on the primer length and specificity. Typical cycle conditions for both high and low stringency amplifications include a denaturation phase of 90-95° C. for 30 sec to 2 min, an annealing phase lasting 30 sec to 2 min, and an extension phase of about 72° C. for 1-2 min. Protocols and guidelines for low and high stringency amplification reactions are found in the art.

The term "about" is used herein to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When not used in conjunction closed wording in the claims or specifically noted otherwise, the words "a" and "an" denote "one or more." The term "conferred by a transgene," for example, thus encompasses one ore more transgene(s).

The terms "comprise," "have," and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any cell or virus that "comprises," "has" or "includes" one or more traits is not limited to possessing only those one or more traits and covers other unlisted traits.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible. As used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

EXAMPLES

Example 1

Amplification of VP2 Gene from Edgar Strain of Infectious Bursal Disease Virus

RNA was isolated from the Edgar strain of infectious bursal disease virus (IBDV). RT-PCR was performed to produce cDNA corresponding to the VP2 gene using the following primers:

```
IBDV VP2 Start NheI:
                                        (SEQ ID NO: 1)
GATCGCTAGCACCATGACAAACCTGCAAGATCAAAC IBDV VP2 end XbaI:
                                        (SEQ ID NO: 2)
GATCTCTAGATCACTACCTCCTTATGGCCCGGATTATG
```

Example 2

Cloning of the VP2 Edgar Gene

The amplified VP2 cDNA product was cloned into pCR 2.1 Topo TA cloning vector (Invitrogen) in a positive orientation as shown in FIG. 1. The VP2 Edgar gene was then digested with NheI and XbaI and transferred into pcDNA3.1, in which the PciI site was disrupted (FIG. 2). The XbaI site present in the primer sequence at the end of the VP2 gene was not functional due to methylation of the bacterial strain used and therefore digestion with XbaI excised a larger fragment using the functional XbaI site present in the pCR 2.1 Topo TA cloning vector. This resulted in the excised fragment containing the entire VP2 open reading frame also having an additional 59 bases containing the multiple cloning sites from the vector (pcDNA3.1 VP2 Edgar).

Example 3

Generation of VP2 E/2512 Gene in pcDNA3.1 Cloning Vector

The hypervariable region of the VP2 gene from the 2512 strain of IBDV was synthesized (Biomatik). The synthetic fragment was then digested with PciI and BamHI and cloned into pcDNA3.1 VP2 Edgar in which the corresponding fragment of the Edgar VP2 gene was removed to generate the pcDNA VP2 E/2512 construct (FIG. 3).

Example 4

Cloning of the HVT UL3/4 Region into pCR Topo TA Vector

A DNA fragment corresponding to positions 12878-14149 of the HVT genome was amplified using Taq polymerase and cloned into the pCR Topo TA cloning vector (Invitrogen) using the following primers:

```
                                    (SEQ ID NO: 3)
HVT > 12878:     AACTGACAGATACAATACG (SEQ ID NO: 4)
HVT < 14149:     CAGCGGATCAATTATATACT
```

HVT numbering is based on Herpesvirus FC126 strain (NCBI Accession No. AF291866.1). A HincII site was present at positions 13385-13386 of the amplified fragment. The left arm of the amplified HVT DNA segment was approximately 507 bp, and the right arm was 765 bp for homologous recombination. The amplified HVT DNA segment in the pCR 2.1 Topo TA vector (pCR Topo TA HVT 12878-14149) is shown in FIG. 4.

Example 5

Cloning the VP2 E/2512 Expression Cassette into HVT Arms

The gene cassette corresponding to VP2 E/2512 with the human cytomegalovirus (CMV) promoter and bovine growth hormone polyA signal was amplified from pcDNA3.1 VP2 E/2512 using PCR and cloned into the HincII (13385-13386) site of the pCR Topo TA HVT 12878-14149. As previously noted, an additional 59-bp fragment remained at the end of the VP2 open reading frame due to the methylation status of the XbaI site.

The primers used for PCR amplification of the VP2 E/2512 expression cassette were as follows:

```
                                    (SEQ ID NO: 5)
pCVM >           CGATGTACGGGCCAGATATAC (SEQ ID NO: 6)
BGHpA <          TCCCCAGCATGCCTGCTATTG
```

FIG. 5 shows the pCR Topo TA HVT 12878-14149 vector containing the inserted elements.

Example 6

HVT Genomic DNA Purification

HVT was propagated in chicken embryonic fibroblasts, and DNA was isolated by standard techniques. The DNA was further treated with RNAse followed by proteinase K to remove contaminating RNA and protein. Aliquots of the purified DNA were frozen at −20° C.

Example 7

Generation of Recombinant HVT Expressing VP2

Secondary chicken embryo fibroblasts were transfected with genomic HVT DNA and VP2 transfer vector using calcium phosphate. Briefly, cells were plated overnight and transfected with 1 µg of genomic DNA and 0.5 µg of VP2 transfer vector when the cells were 80-90% confluent. After 4-5 days of incubation at 37° C. under 5% $CO_2$, the monolayers were overlaid with 1% agar in 2× growth medium. Plaques were isolated using 10× trypsin and plated in duplicate in 24-well plates. DNA was isolated from one plate to test for the insertion of VP2 into the HVT genome. Approximately 576 individual plaques were examined. Positive clones were propagated in duplicate in 60 mm dishes. These clones were examined for second time for the presence of the VP2 insertion. Two clones were identified that stably expressed the VP2 gene after 2 rounds of propagation. One of the clones was identified and re-plaque purified. The resulting cloned HVT-VP2 E2512 was used to make virus stocks. Primers for detection of the VP2 gene in HVT-E2512 recombinants are as follows:

```
                                    (SEQ ID NO: 7)
rVP2 > 628:      GCAGCCGATGACTACCAGT (SEQ ID NO: 8)
rVP2 < 988:      TTGCTGACCATGACATTTGGT
```

Example 8

In Ovo Administration of HVT-IBD VP2, HVT-IBD VP2+NDV(F) and HVT-IBD VP2+NDV(F/HN) Recombinant Construct to Poultry for Protection Against IBDV Strain STC To determine the efficacy of HVT-IBD VP2, HVT-IBD VP2+NDV(F) and HVT-IBD VP2+NDV(F/HN) recombinant constructs against infectious bursal disease (IBD) challenge performed at 28 days of age, specific pathogen-free (SPF) leghorn chicken embryos were allocated into five groups on day 3. Two groups (T01 and T02) were non-vaccinated, Groups T03 were vaccinated in ovo on day 18 of incubation with a target dose of 1500 pfu of HVT-IBD VP2, HVT-IBD VP2+NDV(F) and HVT-IBD VP2+NDV(F/HN), respectively. Eggs were transferred to hatchers according to group. The percent hatch was determined for each group (day 0), and birds were placed in isolation cages by treatment according to the randomization and monitored daily. On day 28 after hatch, 16 birds in each group were bled to determine antibody titer to IBDV, and a different set of 20 birds per group were challenged with the virulent classic IBDV strain STC, given by eye-drop administration. Post-challenge birds were monitored for clinical signs and were euthanized and necropsied four days post challenge for acute gross lesions of the bursa of Fabricius associated with IBD, including edema, peri-bursal edema, and hemorrhage. Birds that died post-challenge and those with acute lesions of IBD at final necropsy were considered susceptible to IBDV. Seroconversion for IBDV was determined using a commercial ELISA (Synbiotics, IBD plus), and birds were considered positive for antibody to IBDV per the manufacturer's specifications.

TABLE 1

Percent hatch and pre-challenge mortality to day 28

| Group | Treatment | Number normal hatched/Number normal embryos transferred | Percent hatched | Number dead/ number placed (Day 0 to Day 28) | Percent Mortality (Day 0 to Day 28) |
| --- | --- | --- | --- | --- | --- |
| T01 | Non-vaccinated | 139/150 | 92.7 | 0/44 | 0.0 |
| T02 | Non-vaccinated | 140/148 | 94.6 | 0/44 | 0.0 |
| T03 | HVT-IBD VP2 | 137/150 | 91.3 | 0/44 | 0.0 |
| T04 | HVT-IBD VP2 + NDV F | 145/150 | 96.7 | 0/44 | 0.0 |
| T05 | HVT-IBD VP2 + NDV F/HN | 143/149 | 96.0 | 1/44 | 2.3 |

Percent hatch was similar for vaccinated and non-vaccinated groups. Clinical signs associated with Marek's disease virus (MDV) or IBDV were not seen in vaccinates, including the one bird that dies post-hatch. These data indicated that the HVT-IBD VP2, HVT-IBD+NDV F and HVT-IBD+NDV F/HN were safe for in ovo administration.

VP2 expression cassette and an expression cassette for NDV proteins F and HN. Ninety-five percent of the birds of T05 were protected from the virulent IBDV challenge. On day 28 post hatch, 93.8% of T03 birds, 100% of T04 birds and 100% of T05 birds were seropositive for antibody to IBDV by ELISA. Therefore, in ovo administered HVT-IBD VP2, HVT-IBD+NDV F and HVT-IBD+NDV F/HN constructs were able to stimulate protective immunity and an IBDV-specific antibody response in SPF chickens.

Example 9

Subcutaneous Administration of HVT-IBDV VP2 Recombinant Construct to Poultry at Hatch for Protection Against IBDV Strain STC To determine the efficacy of HVT-IBD VP2 recombinant construct against IBDV challenge performed at day 28 of age, SPF leghorn chickens were allocated into three groups on day 0. Two groups (T01 and T02) were non-vaccinated and the third group (T03) was vaccinated with a target dose of 1500 pfu HVT-IBD VP2 subcutaneously in the nape on the day of hatch. Birds were placed in isolation cages by treatment according to the randomization and monitored daily. On day 28, 16 birds in each group were bled to

TABLE 2

Percent protection from IBDV challenge and percent seroconversion for VP2 on day 28

| Group | Treatment | IBDV Challenge | Number susceptible/ Number challenged | Percent Susceptible | Number seropositive/ Number sampled | Percent seropositive (Day 28) |
| --- | --- | --- | --- | --- | --- | --- |
| T01 | Non-vaccinated | No | 0/20 | 0.0 | 1/16 | 6.3% |
| T02 | Non-vaccinated | Yes | 19/20 | 95.0 | 1/16 | 6.3% |
| T03 | HVT-IBD VP2 | Yes | 1/20 | 5.0 | 15/16 | 93.8% |
| T04 | HVT-IBD VP2 + NDV F | Yes | 3/20 | 15.0 | 16/16 | 100.0% |
| T05 | HVT-IBD VP2 + NDV F/HN | Yes | 1/20 | 5.0 | 16/16 | 100.0% |

Non-vaccinated challenged chickens were highly susceptible to IBDV, validating the severity of the challenge. Ninety-five percent of the chickens vaccinated in ovo with HVT-IBD VP2 were protected from the virulent IBDV challenge. Birds of treatment T04 were vaccinated with HVT vector construct containing IBDV VP2 expression cassette and an expression cassette for NDV protein F. Eighty-five percent of the birds in T04 were protected from the virulent IBDV challenge. Birds of treatment T05 were vaccinated with HVT vector construct containing IBDV determine antibody titer to IBDV, and 20 birds per group were challenged with the virulent classic IBDV strain STC given by eye-drop administration. Post-challenge birds were monitored for clinical signs and were euthanized and necropsied four days post challenge for acute gross lesions as described in Example 8. Birds that died post-challenge and those with acute lesions of IBD at final necropsy were considered susceptible to IBDV. Seroconversion for IBDV was determined using a commercial ELISA (Synbiotics, IBD plus), and birds were considered positive for antibody to IBDV per the manufacturer's specifications.

TABLE 3

Percent protection from IBDV challenge and percent seroconversion on day 28

| Group | Treatment | IBDV Challenge | Number susceptible/ Number challenged | Percent Susceptible | Number seropositive/ Number sampled | Percent seropositive (Day 28) |
|---|---|---|---|---|---|---|
| T01 | Non-vaccinated | No | 0/20 | 0.0 | 0/16 | 0.0 |
| T02 | Non-vaccinated | Yes | 19/19 | 100.0 | 0/16 | 0.0 |
| T03 | HVT-IBD VP2 | Yes | 2/18 | 11.1 | 15/16 | 93.8% |

Non-vaccinated challenged chickens were highly susceptible to IBDV, as 100% showed signs of IBD, validating the severity of the challenge. Eight-nine percent of the chickens vaccinated at hatch with HVT-IBD VP2 were protected from the virulent challenge. On day 28 post-hatch, 15 of 16 chickens sampled were seropositive for antibody to IBDV. Therefore, the HVT-IBD VP2 construct administered to chickens at hatch was able to stimulate protective immunity and a specific IBDV antibody response in SPF chickens.

Example 10

In Ovo Administration of HVT-IBDV VP2 Recombinant Construct to Poultry for Protection Against MDV Strain GA22

To determine the efficacy of HVT-IBD VP2 recombinant construct against MDV challenge performed at 5 days of age. On Day 3, SPF leghorn chicken embryos were allocated into two groups. One group was non-vaccinated and the other group was vaccinated with a target dose of 1300 pfu HVT-IBD VP2 in ovo on day 18 of incubation. Eggs were transferred to hatchers according to group. On Day 0 birds were placed in isolation cages by treatment according to the randomization. On Day 5 of age birds in each group were challenged with virulent MDV strain GA22. Birds were monitored daily until Day 54 of age at which time they were euthanized and necropsied for gross lesions associated with Marek's disease. Birds dying during the course of the study were necropsied for gross lesions associated with Marek's disease.

TABLE 4

Percent protection from MDV challenge

| Treatment | MDV Challenge | Number dead/ Number challenged (Day 5 to 54) | Percent Dead | Number susceptible/ Number challenged | Percent Susceptible |
|---|---|---|---|---|---|
| Non-vaccinated | Yes | 12/30 | 40.0% | 24/30 | 80.0% |
| HVT-IBD VP2 | Yes | 1/30 | 3.3% | 2/30 | 6.7% |

Eighty percent of the non-vaccinated challenge group was susceptible to MDV, and 40% of these birds died from the challenge prior to the necropsy on day 54, validating the severity of the challenge. Chickens vaccinated with HVT-IBD VP2 in ovo were well protected when challenged with virulent MDV strain GA22, as only 2 of 30 (6.7%) birds were susceptible. Therefore, the HVT-IBD VP2 recombinant vector was able to stimulate strong protective immunity to MD in chickens challenged with virulent MDV.

Example 11

Seroconversion of Broiler Chickens with High Levels of Maternal Immunity Given HVT Expressing IBDV VP2 Recombinant Vector in Ovo To determine seroconversion for IBDV in broiler chickens vaccinated in ovo with HVT-IBD VP2 recombinant construct, commercial broiler chicken embryos were allocated into two groups on day 3 of incubation. One group was non-vaccinated, and the other group was vaccinated with a target dose of 4000 pfu HVT-IBD VP2 in ovo on day 18 of incubation. Eggs were transferred to hatchers according to group. The percent hatch was determined for each group on day 0, and birds were placed in isolation pens by treatment according to the randomization and monitored daily. Birds were bled and serum was collected on days 0, 14, 20, 28, 35, 41, 49, and 56. Seroconversion for IBDV was determined using a commercial ELISA (Synbiotics, IBD plus) and per the manufacturer's instructions.

TABLE 5

Percent hatch and pre-challenge mortality to day 56 of commercial broiler chickens

| Treatment | Number normal hatched/Number normal embryos transferred | Percent hatched | Number dead/ number placed (Day 0 to Day 56) | Percent Mortality (Day 0 to Day 56) |
|---|---|---|---|---|
| Non-vaccinated | 85/91 | 93.4 | 1/25 | 4.0 |
| HVT-IBD VP2 | 76/83 | 91.6 | 1/25 | 4.0 |

Percent hatch and post-hatch mortality were similar for vaccinated and non-vaccinated groups. Clinical signs associated with MDV or IBDV were not seen in vaccinates. These data indicate that the HVT-IBD VP2 was safe for in ovo administration.

TABLE 6

ELISA antibody titers of IBDV in commercial broiler chickens vaccinated in ovo with HVT-IBD VP2 recombinant vector

| Treatment | Group Mean Antibody Titer to IBDV on Day | | | | | | | |
|---|---|---|---|---|---|---|---|---|
| | 0 | 14 | 20 | 28 | 35 | 41 | 49 | 56 |
| Non-vaccinated | 18822 | 10655 | 6712 | 1234 | 498 | 62 | 7 | 6 |
| HVT-IBD VP2 | NT | 3099 | 4779 | 6079 | 7469 | 8778 | 11292 | 15108 |

NT = not tested

These data show that the commercial broiler chickens used in this study had very high levels of maternal immunity to IBDV on the day of hatch, with a titer of 18,822. On day 35, maternal antibody to IBDV was still detectable in the serum of the non-vaccinated chickens. In ovo vaccination with HVT-IBD VP2 recombinant vector stimulated antibody to IBDV that was first evident at 28 days of age. On day 28, the group mean antibody titer for vaccinated chickens was 6079, which was well above the 1234 value determined for the non-vaccinated group. After day 35, maternal immunity to IBDV continued to decline in the non-vaccinated group to near zero by day 56, while the mean titer for birds vaccinated with HVT-IBD VP2 continued to increase through day 56. Therefore, the HVT-IBD VP2 recombinant vector stimulated a strong immune response in commercial broiler chickens with high levels of maternal immunity.

Example 12

Seroconversion and Protection of Broiler Chickens with High Levels of Maternal Immunity Given HVT Expressing IBDV VP2 Recombinant Vector in Ovo To determine seroconversion for IBDV and protection from a virulent IBDV challenge in broiler chickens vaccinated in ovo with HVT-IBD VP2, commercial broiler chicken embryos were allocated into two groups on day 3. One group was non-vaccinated, while chickens in the other group were vaccinated with a target dose of 4000 pfu HVT-IBD VP2 in ovo on day 18 of incubation. Eggs were transferred to hatchers according to vaccination status. The percent hatch was determined on day 0 for both groups, and birds were placed in isolation pens by treatment according to the randomization and monitored daily. Birds were bled and serum collected on days 0, 14, 21, 28, 35, 42, 49, and 55. Seroconversion for IBDV was determined using a commercial ELISA (Synbiotics, IBD plus) per the manufacturer's instructions. Fifteen vaccinated and 15 non-vaccinated birds were challenged on days 27 and 56 with the virulent classic IBDV strain STC by eye-drop administration. Post-challenge birds were monitored for clinical signs and were euthanized and necropsied four days post challenge along with 10 non-vaccinated, non-challenged birds for acute gross lesions of the bursa of Fabricius associated with IBD, including edema, peri-bursal edema, and hemorrhage. Birds that died post-challenge and those with acute lesions of IBD were considered susceptible to IBDV.

TABLE 7

Percent hatch and pre-challenge mortality up to day 56 using commercial broiler chickens

| Treatment | Number normal hatched/Number normal embryos transferred | Percent hatched | Number dead/ number placed (Day 0 to Day 56) | Percent Mortality (Day 0 to Day 56) |
|---|---|---|---|---|
| Non-vaccinated | 110/124 | 88.7 | 3/54 | 5.6 |
| HVT-IBD VP2 | 92/100 | 92.0 | 0/60 | 0.0 |

Percent hatch was similar for vaccinated and non-vaccinated groups. No birds died post-hatch in the HVT-IBD VP2 recombinant vector-treated group. These data indicate that the HVT-IBD VP2 recombinant vector was safe for in ovo administration.

TABLE 8

ELISA antibody titers to IBDV in commercial broiler chickens vaccinated in ovo with HVT-IBD VP2

| Treatment | Group Mean Antibody Titer to IBDV on Day | | | | | | | |
|---|---|---|---|---|---|---|---|---|
| | 0 | 14 | 21 | 28 | 35 | 42 | 49 | 55 |
| Non-vaccinated | 20213 | 18762 | 12517 | 9101 | 4642 | 1334 | 96 | 16 |
| HVT-IBD VP2 | NT | 18761 | 12031 | 9827 | 6502 | 7439 | 10162 | 11440 |

NT = not tested

TABLE 9

Percent protection from IBDV challenges on days 27 and 56

| Treatment | IBDV Challenge | Percent Susceptible Day 27 | Percent Susceptible Day 56 |
|---|---|---|---|
| Non-vaccinated | No | 0.0 | 0.0 |
| Non-vaccinated | Yes | 33.3 | 61.5 |
| HVT-IBD VP2 | Yes | 0.0 | 0.0 |

These data show that the commercial broiler chickens used in this study had very high levels of maternal immunity to IBDV on day of hatch with a titer of 20,213. On day 42, maternal antibody to IBDV was still detectable in the serum of non-vaccinated chickens. In ovo vaccination with HVT-IBD VP2 recombinant vector stimulated antibody to IBDV that was first evident on day 35 of age. On day 35, the group mean antibody titer to IBDV of the vaccinated birds was 6502, which was greater than the 4642 of the non-vaccinated group. After day 35, maternal immunity to IBDV continued to decline in the non-vaccinated group to near zero by day 55, while the mean titer for the group of birds vaccinated with HVT-IBD VP2 increased through day 55. On Day 27, 15 non-vaccinated and 15 vaccinated chickens were challenged with virulent IBDV. Maternal immunity was still high at day 27, which affected the susceptibility of the non-vaccinated challenged chickens, as only 33.3% of chickens in this group were susceptible. None of the birds in the vaccinated group were susceptible to virulent IBDV at day 27. On day 56, 13 non-vaccinated and 14 vaccinated chickens were challenged with virulent IBDV. The non-vaccinated, challenged group had a susceptibility rate of 61.5%, while none of the birds in the vaccinated group were susceptible to virulent IBDV. Therefore, the HVT-IBD recombinant vector stimulated a strong antibody response to IBDV that continued to increase up to day 55. When challenged on days 27 and 55, birds in the vaccinated group were protected from disease and lesions caused by virulent IBDV.

Example 13

Construction of HVT86 (US10) HVT87 (Sorf3) Recombination Region

The HVT genome (AF291988.1) corresponding to genomic positions 137667-138771 and 138772-140634 was PCR-amplified and cloned to generate pUS10-sorf3. Regulatory sequences corresponding to the cytomegalovirus immediate early (IE) promoter and the bovine growth hormone polyA region was PCR amplified using:

```
                                          (SEQ ID NO: 5)
PCVM:         CGATGTACGGGCCAGATATAC (SEQ ID NO: 6)
BGH pA:       TCCCCAGCATGCCTGCTATTG
```

The DNA fragment corresponding to regulatory sequences was cloned into pUS10-sorf3 vector between HVT genome at position 138771-138772 to pUS10-CVM-pA-sorf3 vector Example 14

Cloning of NDV Genes into pUS10-CVM-pA-Sorf3

F Gene Cloning:
The Lasota strain of Newcastle disease virus was amplified using reverse transcriptase PCR (RT-PCR) using the following primers:

```
NDV F > start NheI:
                                          (SEQ ID NO: 9)
GCTAGCATGGGCTCCAGACCTTCTAC
```

```
NDV F > end XbaI:
                                          (SEQ ID NO: 10)
TCTAGATCACATTTTTGTAGTGGCTCTCATCTGATCGAGAGTATTCCCA

AGCC
```

The resulting PCR product was digested with NheI and XbaI and cloned into the corresponding sites in pus10-CVM-pA-sorf3 to generate F gene transfer vector.

HN Gene Cloning:
The Lasota strain of Newcastle disease virus was amplified using reverse transcriptase PCR (RT-PCR) using the following primers:

```
NDV HN start > XbaI:
                                          (SEQ ID NO: 11)
GATATCTCTAGAATGGACCGCGCCGTTAGCC NDV HN end < XbaI:
                                          (SEQ ID NO: 12)
GATATCTCTAGACTAGCCAGACCTGGCTTCTC
```

The resulting PCR product was digested with XbaI and cloned into the corresponding sites in pus10-CVM-pA-sorf3 to generate HN gene transfer vector.

F-P2A-HN Gene Cloning:
The Lasota strain of Newcastle disease virus was amplified using reverse transcriptase PCR (RT-PCR) using the following primers:

```
NDV F > start NheI:
                                          (SEQ ID NO: 9)
GCTAGCATGGGCTCCAGACCTTCTAC NDV F-P2A end < Xba:
                                          (SEQ ID NO: 13)
CATTCTAGATCCGCTTCCAGGTCCAGGGTTCTCCTCCACGTCTCCAGCC

TGCTTCAGCAGGCTGAAGTTAGTAGCTCCGCTTCCCATTTTTGTAGTGG

CTCTCAT
```

The resulting PCR product was digested with NheI and XbaI and cloned into the corresponding sites pus10-CVM-pA-sorf3 vector to generate pus10-CVM-pA-sorf3-F-P2A. The XbaI fragment corresponding to the HN gene of NDV was cloned in frame into pus10-CVM-pA-sorf3-F-P2A to generate F-P2A-HN gene transfer vector. The resulting transfer vector has a 2A peptide derived from porcine Teschovirus-1.

Example 15

Insertion of NDV Genes into HVT Genome

Homologous recombination was used to generate recombinants in which the foreign genes were inserted between US10 and sorf3 (HVT position 138771). Briefly one microgram of HVT infected chicken embryo fibroblasts and 0.5-1 microgram of transfer vector were transfected into chicken embryo fibroblasts using calcium phosphate method. Five days later HVT plaques were purified and examined for presence of foreign gene insertion. The positive clones were further propagated and plaque purified to examine stability and expression of foreign genes.

To generate double recombinants, HVT-VP2 genomic DNA was transfected instead of HVT to generate HVT vector expression VP2 between UL3-UL4 and NDV genes (F, HN or F/HN) at position US10-sorf3.

Example 16

Subcutaneous at Hatch Administration of HVT-IBD VP2+NDV(F) Recombinant Construct to Poultry for Protection Against IBDV Strain STC To determine the efficacy of HVT-IBD VP2+NDV(F) recombinant construct against infectious bursal disease (IBD) challenge performed at 28 days of age, specific pathogen-free (SPF) leghorn chicks were allocated into three groups. Two groups (T01 and T02) were non-vaccinated, Group T03 was vaccinated subcutaneous at hatch with a target dose of 5000 pfu of HVT-IBD VP2+NDV(F). Thirty-two chicks per treatment were placed in isolation cages by treatment and according to the randomization. Birds were monitored daily. On day 28 after hatch, all birds in each group were bled and challenged with the virulent classic IBDV strain STC, given by eye-drop administration. Post-challenge birds were monitored for clinical signs and were euthanized and necropsied four days post challenge for acute gross lesions of the bursa of Fabricius associated with IBD, including edema, peri-bursal edema, and hemorrhage. Birds that died post-challenge and those with acute lesions of IBD at final necropsy were considered susceptible to IBDV. Seroconversion for IBDV was determined using a commercial ELISA (Synbiotics, IBD plus), and birds were considered positive for antibody to IBDV per the manufacturer's specifications.

TABLE 10

Percent protection from IBDV challenge and percent seroconversion on day 28

| Group | Treatment | IBDV Challenge | Number susceptible/ Number challenged | Percent Susceptible | Number seropositive/ Number sampled | Percent seropositive (Day 28) |
|---|---|---|---|---|---|---|
| T01 | Non-vaccinated | No | 0/31 | 0.0 | 2/31 | 6.5% |
| T02 | Non-vaccinated | Yes | 32/32 | 100.0 | 1/32 | 3.1% |
| T03 | HVT-IBD VP2 + NDV F | Yes | 4/31 | 12.9 | 31/31 | 100.0% |

Non-vaccinated challenged chickens were highly susceptible to IBDV, validating the severity of the challenge. Eight-seven percent of the chickens vaccinated subcutaneous at hatch HVT-IBD VP2+NDV(F) were protected from the virulent IBDV challenge. On day 28 post hatch, 100% of T03 birds were seropositive for antibody to IBDV by ELISA. Therefore, subcutaneous administered HVT-IBD VP2+NDV(F) was able to stimulate protective immunity and an IBDV-specific antibody response in SPF chickens.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A recombinant viral vector comprising at least one transgene inserted into a Marek's disease viral genome in an intergenic region flanked by HVT10 (UL3) and HVT11 (UL4) in the unique long region of the genome.

2. A recombinant viral vector comprising at least one transgene inserted into a Marek's disease viral genome in a region selected from the group consisting of:
   (a) an intergenic region flanked by HVT10 (UL3) and HVT11 (UL4) in the unique long region of the genome; and
   (b) an intergenic region flanked by HVT86 (US10) and HVT87 (Sorf3) in the unique short region of the genome.

3. The recombinant viral vector of claim 2, wherein the at least one transgene expresses an antigenic viral gene.

4. The recombinant viral vector of claim 2, wherein the at least one transgene comprises a first transgene inserted into the intergenic region flanked by HVT10 (UL3) and HVT11 (UL4) in the unique long region of the genome, and a second transgene inserted into the intergenic region flanked by HVT86 (US10) and HVT87 (Sorf3) in the unique short region of the genome.

5. The recombinant viral vector of claim 2, wherein the at least one transgene comprises more than one transgene inserted in both the intergenic region flanked by HVT10 (UL3) and HVT11 (UL4) in the unique long region of the genome, and the intergenic region flanked by HVT86 (US10) and HVT87 (Sorf3) in the unique short region of the genome.

6. The recombinant viral vector of claim 3, wherein the antigenic viral gene comprises a gene selected from the group consisting of an infectious bursal disease virus gene, a Newcastle disease virus gene, an avian influenza virus gene, and an infectious laryngotracheitis virus gene.

7. The recombinant viral vector of claim 6, wherein the infectious bursal disease virus gene is a VP2 gene, or the Newcastle disease virus gene is an F gene or an HN gene or an F/HN chimera.

8. The recombinant viral vector of claim 2, wherein the at least one transgene is operatively linked to a heterologous promoter.

9. The recombinant viral vector of claim 8, wherein the promoter comprises a promoter selected from the group consisting of a human cytomegalovirus IE promoter, a guinea pig CMV promoter, an SV40 promoter, a Pseudorabies Virus promoter, a glycoprotein X promoter, a Herpes Simplex Virus-1 promoter, and a Marek's disease viruses promoters.

10. The recombinant viral vector of claim 9, wherein the promoter comprises a human cytomegalovirus IE promoter.

11. The recombinant viral vector of claim 2, wherein the at least one transgene is operatively linked to a polyA signal.

12. The recombinant viral vector of claim 11, wherein the polyA signal is selected from the group consisting of a bovine growth hormone polyA signal, an SV40 polyA signal, an AcNPV 1629 ORF poly(A) signal, and an HSV TK polyA signal.

13. The recombinant viral vector of claim 12, wherein the polyA signal is a bovine growth hormone polyA signal.

14. The recombinant viral vector of claim 2, wherein the at least one transgene is inserted into a Marek's disease viral genome in an intergenic region flanked by HVT10 (UL3) and HVT11 (UL4) in the unique long region of the genome.

15. An immunogenic composition comprising the recombinant viral vector of claim 2.

16. The immunogenic composition of claim 15, wherein the at least one transgene comprises a first transgene inserted into the viral genome in an intergenic region flanked by HVT10 (UL3) and HVT11 (UL4) in the unique long region of the genome; and a second transgene inserted into the viral genome in an intergenic region flanked by HVT86 (US10) and HVT87 (Sorf3) in the unique short region of the genome.

17. The immunogenic composition of claim 16, further comprising at least a third transgene conferring protection against a third disease.

18. The immunogenic composition of claim 15, wherein the at least one transgene is operatively linked to a heterologous promoter.

19. The immunogenic composition of claim 16, wherein the first and second transgenes are operatively linked to the same promoter.

20. The immunogenic composition of claim 16, wherein the first transgene is operatively linked to a heterologous promoter and the second transgene is operatively linked to a second heterologous promoter.

21. The immunogenic composition of claim 15, wherein the at least one transgene encodes a viral gene selected from the group consisting of an infectious bursal disease virus gene, a Newcastle disease virus gene, an avian influenza virus gene, and an infectious laryngotracheitis virus gene.

22. The immunogenic composition of claim 21, wherein the infectious bursal disease virus gene is a VP2 gene, or the Newcastle disease virus gene is an F gene or an HN gene or an F/HN chimera.

23. A method for preventing or inhibiting Marek's disease in combination with at least a second disease in poultry, comprising providing the composition of claim 15 to a bird, wherein the composition is provided in an amount effective to prevent or inhibit Marek's disease and the at least a second disease in the bird.

24. The method of claim 23, wherein the composition is provided to the bird by injection.

25. The method of claim 24, wherein the injection is selected from the group consisting of intravenous injection, intramuscular injection, subcutaneous injection, and in ovo injection.

26. The method of claim 23, wherein the composition is provided to the bird prior to infection with or exposure to a disease.

27. The method of claim 23, wherein the bird is a species of poultry.

28. The method of claim 27, where the species of poultry is selected from the group consisting of a chicken, a turkey, a quail, a goose, a duck, a swan, a guinea, and a pigeon.

29. The method of claim 23, wherein the composition is provided to the bird in combination with a non-naturally occurring pharmaceutically acceptable carrier.

\* \* \* \* \*